(12) United States Patent
Minor et al.

(10) Patent No.: US 11,540,731 B2
(45) Date of Patent: Jan. 3, 2023

(54) MEDICAL TREATMENT SYSTEM USING MEASUREMENT DATA FROM MULTIPLE SENSORS

(71) Applicant: W. L. Gore & Associates, Inc., Newark, DE (US)

(72) Inventors: David J. Minor, Phoenix, AZ (US); Benjamin M. Trapp, Phoenix, AZ (US); Christopher J. Vecchio, Philadelphia, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 305 days.

(21) Appl. No.: 16/724,794

(22) Filed: Dec. 23, 2019

(65) Prior Publication Data

US 2020/0196943 A1   Jun. 25, 2020

Related U.S. Application Data

(60) Provisional application No. 62/901,105, filed on Sep. 16, 2019, provisional application No. 62/894,260,
(Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0031* (2013.01); *A61B 5/0205* (2013.01);
(Continued)

(58) Field of Classification Search
CPC . A61B 5/02055; A61B 5/0031; A61B 5/0205; A61B 5/14542; A61B 5/14552;
(Continued)

(56) References Cited

U.S. PATENT DOCUMENTS 5,276,276 A   1/1994   Gunn
5,334,217 A   8/1994   Das
(Continued)

FOREIGN PATENT DOCUMENTS

CN   104414692 A   3/2015
EP   1264572 A1   12/2002
(Continued)

OTHER PUBLICATIONS

International Search Report and Written Opinion received for PCT Patent Application No. PCT/US2019/068277, dated Mar. 25, 2020, 13 pages.
(Continued)

*Primary Examiner* — Brian T Gedeon

(57) ABSTRACT

A medical treatment system for determining administration of medications to a patient is disclosed. The system uses a plurality of sensors to perform a first set of physiologic measurements in a right side of the heart and a second set of physiologic measurements in a left side of the heart. The system also includes a receiver configured to receive measurement data regarding the first and second sets of physiologic measurements and output to a display device the received measurement data.

15 Claims, 14 Drawing Sheets

| LA/RA Pressure Treatment Algorithm | RAP Trending Below Normal | RAP Trending Normal | RAP Trending Above Normal |
|---|---|---|---|
| LAP Trending Below Normal | Reduce Diuretics | Reduce Vasodilators | Reduce Vasodilators |
| LAP Trending Normal | Reduce Diuretics | Hold Meds | Increase Diuretics |
| LAP Trending Above Normal | Increase Vasodilators | Increase Vasodilators | Increase Diuretics |

Related U.S. Application Data filed on Aug. 30, 2019, provisional application No. 62/845,386, filed on May 9, 2019, provisional application No. 62/783,902, filed on Dec. 21, 2018, provisional application No. 62/783,935, filed on Dec. 21, 2018.

(51) Int. Cl.
  *A61B 5/07* (2006.01)
  *A61B 5/1455* (2006.01)
  *A61B 5/145* (2006.01)
  *A61L 31/10* (2006.01)
  *A61B 5/20* (2006.01)
  *A61F 2/24* (2006.01)
  *A61M 27/00* (2006.01)
  *A61B 5/0215* (2006.01)
  *A61B 17/12* (2006.01)
  *A61L 31/00* (2006.01)
  *A61L 31/08* (2006.01)

(52) U.S. Cl.
  CPC .......... *A61B 5/076* (2013.01); *A61B 5/14542* (2013.01); *A61B 5/14552* (2013.01); *A61B 5/201* (2013.01); *A61B 5/486* (2013.01); *A61B 5/4839* (2013.01); *A61B 5/6847* (2013.01); *A61B 5/7275* (2013.01); *A61B 5/742* (2013.01); *A61F 2/2487* (2013.01); *A61L 31/10* (2013.01); *A61M 27/002* (2013.01); *A61B 5/0215* (2013.01); *A61B 5/02158* (2013.01); *A61B 17/12022* (2013.01); *A61B 2560/0219* (2013.01); *A61F 2250/0001* (2013.01); *A61F 2250/0002* (2013.01); *A61F 2250/0069* (2013.01); *A61F 2250/0093* (2013.01); *A61L 31/00* (2013.01); *A61L 31/08* (2013.01); *A61L 2300/236* (2013.01); *A61L 2300/42* (2013.01); *A61M 2205/04* (2013.01); *A61M 2205/3303* (2013.01); *A61M 2205/3331* (2013.01); *A61M 2205/3507* (2013.01)

(58) Field of Classification Search
  CPC ....... A61B 5/201; A61B 5/4838; A61B 5/486; A61B 5/6847; A61B 5/7275; A61B 5/742; A61B 5/0215; A61B 5/02158; A61B 2560/0219; A61F 2/2478; A61F 2250/0001; A61F 2250/0002; A61F 2250/0069; A61F 2250/0093; A61L 31/10; A61L 2300/42; A61L 2300/236
  See application file for complete search history.

(56) References Cited

U.S. PATENT DOCUMENTS

| | | |
|---|---|---|
| 5,683,411 A | 11/1997 | Kavteladze et al. |
| 5,944,738 A | 8/1999 | Amplatz et al. |
| 6,042,602 A | 3/2000 | Wells |
| 6,042,605 A | 3/2000 | Martin et al. |
| 6,077,291 A | 6/2000 | Das |
| 6,080,182 A | 6/2000 | Shaw et al. |
| 6,461,665 B1 | 10/2002 | Scholander |
| 6,911,037 B2 | 6/2005 | Gainor et al. |
| 6,926,670 B2 | 8/2005 | Rich et al. |
| 7,001,409 B2 | 2/2006 | Amplatz |
| 7,049,380 B1 | 5/2006 | Chang et al. |
| 7,236,821 B2 | 6/2007 | Cates et al. |
| 7,462,675 B2 | 12/2008 | Chang et al. |
| 7,871,659 B2 | 1/2011 | Cook et al. |
| 7,887,562 B2 | 2/2011 | Young et al. |
| 7,901,702 B2 | 3/2011 | Schwarz |
| 8,021,331 B2 | 9/2011 | Herweck et al. |
| 8,043,360 B2 | 10/2011 | McNamara et al. |
| 8,048,440 B2 | 11/2011 | Chang et al. |
| 8,480,707 B2 | 7/2013 | Pavcnik et al. |
| 8,545,525 B2 | 10/2013 | Surti et al. |
| 8,696,693 B2 | 4/2014 | Najafi et al. |
| 8,715,300 B2 | 5/2014 | Najafi et al. |
| 8,728,103 B2 | 5/2014 | Surti et al. |
| 9,241,695 B2 | 1/2016 | Peavey et al. |
| 9,314,556 B2 | 4/2016 | Tuseth |
| 9,358,371 B2 | 6/2016 | McNamara et al. |
| 9,399,085 B2 | 7/2016 | Cleek et al. |
| 9,456,812 B2 | 10/2016 | Finch et al. |
| 9,545,300 B2 | 1/2017 | Cully et al. |
| 9,554,786 B2 | 1/2017 | Carley et al. |
| 9,629,715 B2 | 4/2017 | Nitzan et al. |
| 9,636,094 B2 | 5/2017 | Aurilia et al. |
| 9,649,481 B2 | 5/2017 | Sadanand |
| 9,681,948 B2 | 6/2017 | Levi et al. |
| 9,757,107 B2 | 9/2017 | McNamara et al. |
| 9,775,591 B2 | 10/2017 | Delgado et al. |
| 9,861,346 B2 | 1/2018 | Callaghan |
| 9,878,162 B2 | 1/2018 | Mika et al. |
| 9,949,728 B2 | 4/2018 | Cahill |
| 2002/0077556 A1 | 6/2002 | Schwartz |
| 2002/0169475 A1 | 11/2002 | Gainor et al. |
| 2002/0173742 A1 | 11/2002 | Keren et al. |
| 2003/0055344 A1 | 3/2003 | Eigler et al. |
| 2003/0139819 A1 | 7/2003 | Beer et al. |
| 2004/0063805 A1 | 4/2004 | Pacetti et al. |
| 2005/0038351 A1 | 2/2005 | Starobin et al. |
| 2005/0148925 A1 | 7/2005 | Rottenberg et al. |
| 2006/0008500 A1 | 1/2006 | Chavan et al. |
| 2006/0116590 A1 | 6/2006 | Fayram et al. |
| 2006/0198866 A1 | 9/2006 | Chang et al. |
| 2006/0271116 A1 | 11/2006 | Stahmann et al. |
| 2007/0032734 A1 | 2/2007 | Najafi et al. |
| 2007/0118039 A1 | 5/2007 | Bodecker et al. |
| 2007/0282430 A1 | 12/2007 | Thommen et al. |
| 2008/0249562 A1 | 10/2008 | Cahill |
| 2008/0262518 A1 | 10/2008 | Freudenthal |
| 2009/0024042 A1 | 1/2009 | Nunez et al. |
| 2009/0030331 A1 | 1/2009 | Hochareon et al. |
| 2009/0221923 A1 | 9/2009 | Uemura et al. |
| 2010/0049313 A1 | 2/2010 | Alon et al. |
| 2010/0094401 A1 | 4/2010 | Kolbel et al. |
| 2011/0071623 A1 | 3/2011 | Finch et al. |
| 2011/0098767 A1 | 4/2011 | Sugimachi et al. |
| 2011/0295183 A1 | 12/2011 | Finch et al. |
| 2012/0136385 A1 | 5/2012 | Cully |
| 2012/0265296 A1 | 10/2012 | McNamara et al. |
| 2013/0165967 A1 | 6/2013 | Amin et al. |
| 2013/0281988 A1 | 10/2013 | Magnin et al. |
| 2014/0012368 A1 | 1/2014 | Sugimoto et al. |
| 2014/0128795 A1 | 5/2014 | Keren et al. |
| 2014/0142617 A1 | 5/2014 | Larsen et al. |
| 2014/0207153 A1 | 7/2014 | Najafi et al. |
| 2014/0222040 A1 | 8/2014 | Park et al. |
| 2014/0228683 A1 | 8/2014 | Aoki et al. |
| 2014/0343670 A1 | 11/2014 | Bakis et al. |
| 2015/0142049 A1 | 5/2015 | Delgado et al. |
| 2015/0313599 A1 | 11/2015 | Johnson et al. |
| 2016/0058452 A1 | 3/2016 | Brenneman et al. |
| 2016/0263299 A1 | 9/2016 | Xu et al. |
| 2017/0042705 A1 | 2/2017 | Cook et al. |
| 2017/0105711 A1 | 4/2017 | Masters |
| 2017/0106176 A1 | 4/2017 | Taft et al. |
| 2017/0172766 A1 | 6/2017 | Vong et al. |
| 2017/0196673 A1 | 7/2017 | Cully et al. |
| 2017/0281339 A1 | 10/2017 | Levi et al. |
| 2017/0319823 A1 | 11/2017 | Yacoby et al. |
| 2018/0000580 A1 | 1/2018 | Wallace et al. |
| 2018/0008830 A1* | 1/2018 | Kaiser .................. A61B 5/283 |
| 2018/0098772 A1 | 4/2018 | Goldshtein et al. |
| 2018/0280667 A1 | 10/2018 | Keren |
| 2019/0282178 A1 | 9/2019 | Volosin et al. |
| 2020/0038567 A1 | 2/2020 | Siess et al. |
| 2020/0085378 A1 | 3/2020 | Burnett et al. |
| 2020/0179663 A1 | 6/2020 | McDaniel et al. |
| 2020/0196876 A1 | 6/2020 | Minor et al. |

(56) References Cited

U.S. PATENT DOCUMENTS

| | | |
|---|---|---|
| 2020/0196944 A1 | 6/2020 | Minor et al. |
| 2020/0197178 A1 | 6/2020 | Vecchio |
| 2021/0259839 A1 | 8/2021 | Cole et al. |
| 2021/0290214 A1 | 9/2021 | Cole et al. |

FOREIGN PATENT DOCUMENTS

| | | |
|---|---|---|
| EP | 2020248 A1 | 2/2009 |
| EP | 2637576 A1 | 9/2013 |
| GB | 1355373 A | 6/1974 |
| GB | 1506432 A | 4/1978 |
| GB | 1509023 A | 4/1978 |
| JP | 2003-061917 A | 3/2003 |
| JP | 2003-519542 A | 6/2003 |
| JP | 2006-528023 A | 12/2006 |
| JP | 2007-527742 A | 10/2007 |
| JP | 2008-545471 A | 12/2008 |
| JP | 2010-505481 A | 2/2010 |
| JP | 2014-151049 A | 8/2014 |
| JP | 2016-538094 A | 12/2016 |
| JP | 2017-536857 A | 12/2017 |
| WO | 93/13712 A1 | 7/1993 |
| WO | 01/51123 A1 | 7/2001 |
| WO | 2004/091411 A2 | 10/2004 |
| WO | 2005/074367 A2 | 8/2005 |
| WO | 2006/054343 A1 | 5/2006 |
| WO | 2008/040555 A2 | 4/2008 |
| WO | 2009/137755 A2 | 11/2009 |
| WO | 2012/091809 A1 | 7/2012 |
| WO | 2014/150106 A1 | 9/2014 |
| WO | 2015/109027 A2 | 7/2015 |
| WO | 2017/118738 A1 | 7/2017 |

OTHER PUBLICATIONS

International Search Report and Written Opinion received for PCT Patent Application No. PCT/US2019/068280, dated Mar. 25, 2020, 12 pages.
International Search Report and Written Opinion received for PCT Patent Application No. PCT/US2019/068282, dated Mar. 25, 2020, 15 pages.
International Search Report and Written Opinion received for PCT Patent Application No. PCT/US2019/042248, dated Oct. 23, 2019, 18 pages.
International Search Report and Written Opinion received for PCT Patent Application No. PCT/US2019/042252, dated Oct. 21, 2019, 18 pages.
International Search Report and Written Opinion received for PCT Patent Application No. PCT/US2021/013411, dated May 6, 2021, 11 pages.
Wei, X., Liu, X., Rosenzweig, A. What do we know about the cardiac benefits of exercise? Trends in Cardiovascular Medicine; 25(6): 537-539. Aug. 2015 (Year: 2015).
Eigler et al., "Cardiac Unloading with an Implantable Interatrial Shunt in Heart Failure: Serial Observations in an Ovine Model of Ischemic Cardiomyopathy", Structural Heart, vol. 1, No. (1-2), 2017, 'pp. 40-48.
Feldman et al., "Transcatheter Interatrial Shunt Device for the Treatment of Heart Failure Rationale and Design of the Randomized Trial to Reduce Elevated Left Atrial Pressure in Heart Failure (Reduce LAP-HF I)", Circulation Heart failure, vol. 9, No. 7, 2016, pp. 1-10.
Gregg et al., "Interatrial Shunting for Heart Failure the V-Wave Shunt", Presentation at the Transcatheter Cardiovascular Therapeutics (TCT) Congress in Denver, Colorado, 2017, 18 pages.
International Preliminary Report on Patentability received for PCT Patent Application No. PCT/US2019/065610, dated Jun. 24, 2021, 9 pages.
International Preliminary Report on Patentability received for PCT Patent Application No. PCT/US2019/068275, dated Jul. 1, 2021, 11 pages.
International Preliminary Report on Patentability received for PCT Patent Application No. PCT/US2019/068277, dated Jul. 1, 2021, 7 pages.
International Preliminary Report on Patentability received for PCT Patent Application No. PCT/US2019/068280, dated Jul. 1, 2021, 7 pages.
International Preliminary Report on Patentability received for PCT Patent Application No. PCT/US2019/068282, dated Jul. 1, 2021, 9 pages.
International Search Report and Written Opinion received for PCT Patent Application No. PCT/US2019/065610, dated Mar. 26, 2020, 12 pages.
International Search Report and Written Opinion received for PCT Patent Application No. PCT/US2019/068275, dated Jun. 25, 2020, 16 pages.
Kapur NK et al. Mechanical circulatory support devices for acute right ventricular failure. Circulation. 2017; 136:314-326 (Year: 2017).
Sondergaard et al., "Transcatheter treatment of heart failure with preserved or mildly reduced ejection fraction using a novel interatrial implant to lower left atrial pressure", European Journal of Heart Failure, vol. 16, 2014, pp. 796-801.

* cited by examiner

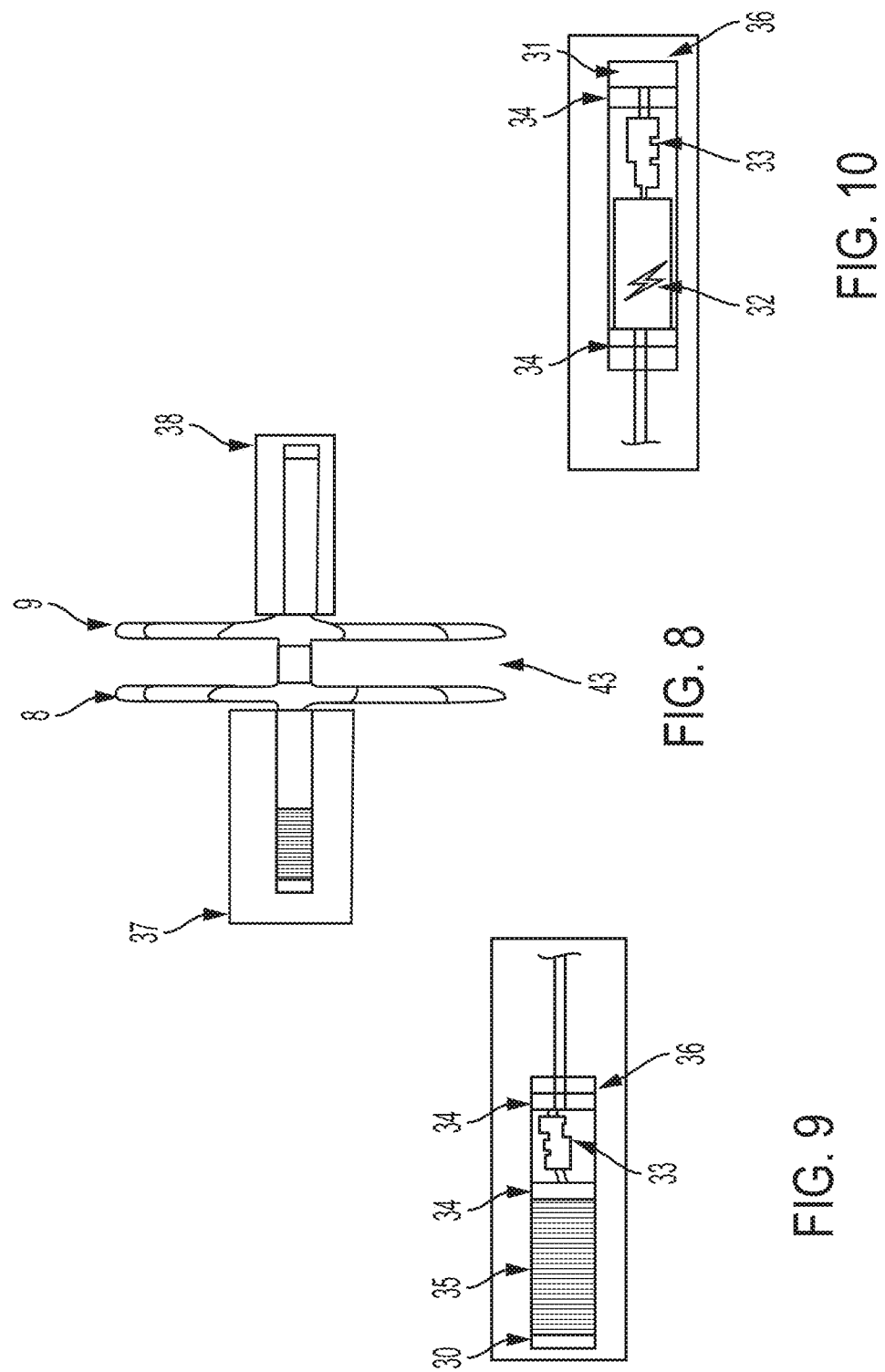

MEDICAL TREATMENT SYSTEM USING MEASUREMENT DATA FROM MULTIPLE SENSORS

CROSS-REFERENCE TO RELATED APPLICATION

This application claims the benefit of Provisional Application No. 62/783,902, filed Dec. 21, 2018, Provisional Application No. 62/783,935, filed Dec. 21, 2018, Provisional Application No. 62/845,386, filed May 9, 2019, Provisional Application No. 62/894,260, filed Aug. 30, 2019, and Provisional Application No. 62/901,105, filed Sep. 16, 2019, all of which are incorporated herein by reference in their entireties for all purposes.

FIELD

The present disclosure relates systems for treating patients, and more specifically to systems and methods for determining administration of medications using physiologic measurements.

BACKGROUND

During the past decade, the number of coronary deaths in the United States has steadily decreased thanks to advancements in medical science and treatment, but the relative number of heart failure deaths has increased, indicating that more people are living with a high risk of heart failure than ever before. Generally, heart failure occurs when the heart cannot supply enough blood to the body. As a result, lower volume output leads to a higher filling pressure in the left heart to help compensate for the lack of output. Lower volume output also causes lower organ perfusion, including a reduction in kidney or renal perfusion. Reduced kidney perfusion can result in a retention of excess fluid. An acute decompensation episode is when fluid levels rise and/or vascular blood distribution declines to a state that causes the patient to experience fatigue and dyspnea (trouble breathing), thus presenting to the hospital. If left untreated, this may result to serious complications and death.

It has been observed that heart failure primarily initiates as a result of left-side heart issues. In a normal healthy heart, oxygenated blood is first carried from the pulmonary veins, through the left atrium, into the left ventricle, and into the aorta, after which the blood is carried throughout the body. Thereafter, deoxygenated blood is carried from the two vena cavae into the right atrium, through the right ventricle, and into the pulmonary arteries, which then carry the blood into the lungs for oxygenation. The pumping performance of the left ventricle can be affected by the thickening/thinning of the left ventricular wall or by the aortic/mitral valve damage, causing less blood to be pumped to the rest of the body.

There are at least two categories of heart failures: HFrEF (heart failure with reduced ejection fraction) and HFpEF (heart failure with preserved ejection fraction). In HFrEF, the left ventricle fills with enough blood, but cannot pump enough blood out due to poor contraction of the heart muscle. This is also called systolic heart failure. In HFpEF, the heart can pump blood out normally, but the left ventricle fills with less blood due to poor relaxation of the heart muscle creating less blood volume in the ventricle. This is also called diastolic heart failure. In either case, there generally is not enough blood being pumped to the body. Less commonly, biventricular failure can occur, which is when the left heart cannot pump enough blood out to the body and the right heart cannot pump enough blood to the lungs.

Pharmacological treatments are commonly employed to reduce heart pressure and prevent acute decompensation episodes. Remotely, the particular drug used is often determined by a trial and error approach using sign/symptoms such as weight gain, or by a singular intra-cardiac blood pressure measurement. Medications that are used today to reduce heart pressure and prevent acute decompensation episodes primarily include diuretics and vasodilators (nitrates, hydralazine, ace inhibitors, etc.) while other medications can be beta-blockers, inotropes, and more. Diuretics primarily target excess fluid buildup (fluid retention) and work by making the kidney release more sodium into the urine. The sodium then takes water with it from the bloodstream, thereby decreasing the amount of fluid flowing through the blood vessels and ultimately reducing blood pressure. Loop diuretics, which are common in chronic heart failure, are also known to have a vasodilator effect on the venous vasculature, causing an increase in venous capacitance. Therefore, diuretics primarily help lower the preload on the heart by reducing blood volume from circulation.

Vasodilators are medications that open or dilate blood vessels, which can include nitrates, hydralazine, ace-inhibitors, and angiotensin receptor blockers, to name a few. As a result, blood flows more easily through the vessels, primarily arterial resistance vessels, and the heart does not need to pump as hard, thereby reducing intra-cardiac blood pressure. Nitrates, for example, are venous dilators at very low initial doses, but primarily increasingly affect arterial dilation in moderate to high doses (typical dosage of heart failure). Unlike diuretics, vasodilator therapy is primarily used to help reduce vascular resistance and afterload on the heart, which enhances stroke volume and cardiac output and leads to secondary decreases in left ventricular preload and venous pressures resulting in lower left sided filling pressure. Beta-blockers work to make the heart pump slower, i.e. induces lower heart rate, and with less force, thereby reducing blood pressure. Inotropes work to increase the strength of ventricular contraction and therefore increase the heart rate. This medication is used in severe cases where extremely poor perfusion exists and a ventricular assist device (VAD) or heart transplant is needed. Generally, when a remote monitoring system indicates a rise in intra-cardiac pressure, the rise signals the need for one of the aforesaid medications to be added or the dosage of said medications to be increased, in order to reduce the intracardiac blood filling pressure. Increasing the dosage of the medications to keep down the intracardiac filling pressure before it gets too high is thought to be the key to reduce the number of hospitalizations.

Early preventative analyses have been proven to be effective in reducing rehospitalizations due to heart failure. As shown in FIG. 1A, by monitoring the predictive biomarkers and performing the appropriate early interventions, the risk of rehospitalization in a patient is significantly lowered. For example, in the earliest stages preceding a potential hospitalization event when the heart is hemodynamically stable, using measurement devices to measure an increase in the filling pressure of the heart can treat the earliest symptoms. Afterwards, when the heart experiences pre-symptomatic congestion, the intrathoracic impedance changes. Later, other signs like a sudden weight gain, swelling in the feet and ankles, weakness or shortness of breath (dyspnea), and changes in the frequency of urination show that the body is retaining fluid. At this stage, however, the disease is already at a later stage that is dangerously close to a decompensation of vital organs in the body, which in many cases include the kidneys. Therefore, it is best to treat the earliest symptoms because when the patient experiences the later symptoms that occur prior to a decompensation episode, it may be too late and permanent damages may have already been done to the organs.

To understand and treat a patient's heart failure, the hospital performs many acute analyses using various means of measurements. These include noninvasive measurements as well as invasive ones so that the medical service providers can get a better understanding of the patient's disease. Noninvasive measurements include: echocardiogram, which is used to diagnose the disease, monitor blood flow, and visualize changes in physiology; weight gain, which determines changes in fluid retention; visual inspection of the jugular vein, which determines fluid retention status; blood pressure readings, which estimate the blood flow of the body; heart rate; electrocardiography (ECG); and oxygen saturation. Invasive measurements include: right heart catheterization and left heart catheterization.

Right heart catheterization, which is performed using Swan-Ganz catheterization, can measure the central venous pressure, right atrial pressure (RAP), right ventricular diastolic and systolic pressures, pulmonary arterial diastolic and systolic pressures, and pulmonary artery wedge pressure (PAWP). Also, this method can measure the oxygen status, temperature, and heart rate of the patient, as well as calculate the cardiac output, systemic vascular resistance, and pulmonary vascular resistance. The right heart catheterization is primarily used to check pressures, cardiac output, resistance, and fluid status in the heart. Left heart catheterization can measure the left atrial pressure as well as the left ventricular diastolic and systolic pressures. The right heart catheterization can be left in a patient for a few days while the medical service providers attempt to reduce the patient's intracardiac blood filling pressure back to acceptable levels using medications. This is an effective practice in an acute setting. During the ESCAPE clinical trial, the use of pressure measurements was determined as a viable means to improve a patient's overall status in the acute setting, for example by targeting a RAP of ≤8 mm Hg and a PAWP of ≤15 mm Hg. However, it was not an ongoing solution, and therefore did not prevent rehospitalizations because the pressures were assumed to change relatively shortly after leaving the hospital. Therefore, a right heart catheter is primarily used to guide therapy to reduce symptoms and pressure in the acute setting.

As such, there is a need for a more convenient but accurate means of measuring the blood pressure within the heart. Current art in the field can be divided into two broad settings: acute and remote. The acute setting is where a patient is in a hospital and assessed using various methods (invasive or noninvasive) as discussed above, in a one-time event, in which the patient is sitting down or lying down in a stationary manner while these tests and measurements are performed. The remote setting is where the patient's pressure readings are done outside the hospital, such as at home, and medications are adjusted in this setting.

In the acute setting, a right heart catherization gives the medical service providers the information they need to choose the right medications for the patient to reduce symptoms. Primarily, it is very useful in separating the effects of fluid retention and fluid distribution. This is done by observing both the PAWP and the right atrial pressures together. Medical service providers will look at the absolute values and ratios to distinguish between the two issues, particularly in the left heart failure, such that they know when fluid is offloaded and are then able to determine the status of the blood distribution. In current practice, the acute setting allows for the most accurate measurement of the heart's health because pressure readings from different locations within the heart are taken into consideration simultaneously. In contrast, the remote cardiac pressure sensors which are currently commercially available only report a single pressure measurement.

FIG. 1B is illustrative of how a right heart catheterization is implemented. The measurement device 40 is attached to the end of a pulmonary artery catheter 18 which passes through the right atrium 1, the tricuspid valve 7, the right ventricle 2, through the pulmonary valve 58, and into the pulmonary artery 16 where the device 40 takes measurement of the blood pressure as deoxygenated blood is carried into the lung 22. Then, fresh air is carried into the lung 22 from the trachea 23 after which oxygenated blood is carried through the pulmonary vein 17, the left atrium 3, the mitral valve 6, the left ventricle 4, and the aortic valve 57. The catheter 18 also has a proximal injection port which injects cold saline bolus 20 into the right atrium, and a thermistor 21 located at a distal end of the catheter to measure the temperature of the blood in the pulmonary artery 16. This method of measurement is known as thermodilution, which measures the blood flow based on the premise that when the cold saline bolus is added to the circulating blood, the rate of blood flow is inversely proportional to the rate of change in blood temperature resulting from the cold saline bolus over time. This provides a measure of cardiac output.

Pulmonary artery wedge pressure and pulmonary artery diastolic is a surrogate measurement for the pressure within the left ventricle, which is a typical area of concern in heart failure. It has been shown that the pulmonary artery and left ventricular filling pressures correlate on most occasions except for certain comorbidities such as primary pulmonary arterial hypertension. Such pressures change because of circulating volume increase (fluid retention) or declining pumping efficiency of the left ventricle (e.g., thickening, dilation, or vasoconstriction of the peripheral resistance vessels).

Various attempts have been made to remotely monitor cardiac pressures in order to identify more effective pharmacological treatment programs. These systems seek monitor increases in intracardiac pressures to provide an early predictor of an impending acute decompensation for a patient with prior history of heart failure (e.g., as a much more reliable indicator than other measurements such as weight gain, thoracic impedance, etc.) For example, the CardioMEMS™ heart failure monitoring system by Abbott resides in the pulmonary artery and seeks to effectively monitor pulmonary artery pressures as a surrogate for left atrial pressure.

Other examples of remote monitoring systems known in the art include: Chronicle® by Medtronic and HeartPOD™ by Abbott/St. Jude. A short overview of each of these prior-art devices is provided below.

With Chronicle®, the measurement device resides in the right ventricle and reports an estimated pulmonary artery diastolic pressure (ePAD) to a receiving device. It has been stated that the measurements showed a correlation between right ventricular diastolic pressure, right ventricular systolic pressure, and ePAD, with the increase in all these pressure readings acting as indicators of an impending hospitalization.

HeartPOD™ uses a lead-and-can design with delivery of a measurement device by septal puncture method, with the measurement device remaining in the atrial septum and measuring left atrial pressure.

Over the past several decades, the prior art has been focused on finding a reliable predictor of an upcoming hospitalization event. Measuring left sided filling pressure and surrogates have demonstrated to be the most predictive and effective means of predicting an upcoming hospitalization event. However, the prior art has not addressed effective management of the patient alongside the prediction. Without signs and symptoms to rely upon, other additional measurements are required to effectively treat the patient with medications and other therapies. Each case of the prior-art devices described above creates a singular confounded measurement because each measurement is able to indicate an early rise in pressure to show that "something" is changing, but the measurement itself is insufficient to define specifically "what" is changing. This can be contrasted to acute right heart catheterization, because with these prior art devices there is not enough data provided to more accurately detect the cause of the problem remotely. This confounding measurement often leaves medical service providers with no other choice but to perform trial-and-error with medications, which may result in ineffective treatment and even cause serious complications in the patient's health. It may also lead to a right heart catheterization procedure to understand what is going on and address the problem in the acute setting.

For example, the medical service providers will first try diuretics to reduce the pressure, if they assume that the pressure increase is due to a fluid retention issue. If this does not work, they may increase the dosage of diuretics again. If this still does not work, the medical service providers may then decide that the problem is not in the fluid retention, but in the fluid distribution, after which they will attempt to use medications such as vasodilators and eventually inotropes. In other words, this method relies heavily on the medical service providers' intuitions which may eventually lead to a correct diagnosis, but at the cost of spending a longer time to do so.

The abovementioned trial-and-error method has a number of drawbacks. Because the heart failure decompensation is a time-based event, which means that blood pressure will rise over time leading to a hospitalization event, every attempt with medication changes has a few days of turnaround time from resulting pressure changes, leaving a relatively small window for error. Also, applying diuretics when there is not enough fluid in the system (in the case of a wrong guess made by the medical service providers) leads to overdiuresis, which can create a hypovolemic state and harm the kidneys. Medical service providers often send the patient to the lab for a creatinine test to assess the health of the kidneys, and if the creatinine levels are outside the normal range for a healthy kidney, the medical service providers then know that damage may have been implicated on the kidneys and that they have performed too much diuresis. More importantly, the longer the pressures remain high, the more likely it is that further damages can occur to the patient's body. For example, the right heart failure may accelerate, the left heart failure may accelerate, the valves within the heart may be damaged, and the kidney failure may accelerate.

In general terms, there is an ongoing need for improved diagnostic system to assist in proper treatment regimens for patients at risk of heart failure hospitalizations based on the physiologic measurements performed.

SUMMARY

Disclosed herein are medical treatment systems and methods for determining administration of medications to a patient based on the measurements performed.

In an Example 1, a medical treatment system for determining administration of medications to a patient, comprises: a plurality of sensors configured to perform a first set of physiologic measurements in a right side of the heart and a second set of physiologic measurements in a left side of the heart; and a receiver configured to receive measurement data regarding the first and second sets of physiologic measurements and output to a display device the received measurement data.

In an Example 2, the medical treatment system of Example 1, the system further comprising: a memory unit configured to store the received measurement data; and a controller configured to determine, based on the received measurement data, whether each of the first and second sets of measurements is: trending lower or higher.

In an Example 3, the medical treatment system of Example 2, wherein the controller is further configured to determine whether to modify a pharmacologic treatment regimen based upon the received measurement data.

In an Example 4, the medical treatment system of either Example 2 or 3, wherein the controller is associated with an implantable measurement device.

In an Example 5, the medical treatment system of any one of Example 2-4, wherein the controller is associated with a monitoring system configured to be located external to the patient.

In an Example 6, the medical treatment system of any one of Examples 1-5, wherein the physiologic measurements include blood pressure measurements.

In an Example 7, the medical treatment system of any one of Examples 1-6, wherein the physiologic measurements include at least one of blood temperature and oxygen saturation measurements.

In an Example 8, a method of assessing a heart failure status of a patient, the method comprising: receiving first measurement data based on a first set of physiologic measurements performed in a right side of a heart of the patient, wherein the first measurement data is transmitted from an implanted measurement system; receiving second measurement data based on a second set of physiologic measurements performed in a left side of the heart, wherein the second measurement data is transmitted from the implanted measurement system; and outputting, to a display device, the received first and second measurement data.

In an Example 9, the method of Example 8, further comprising determining, based on the first and second measurement data, whether each of the first and second sets of physiologic measurements is: trending lower or higher.

In an Example 10, the method of Example 8, further comprising determining whether to modify a pharmacologic treatment regimen based upon the received first and second measurement data.

In an Example 11, the method of any one of Examples 8-10, wherein the implanted measurement system comprises a plurality of sensors, and the first and second sets of physiologic measurements are performed using the plurality of sensors.

In an Example 12, the method of any one of Examples 8-11, wherein the physiologic measurements include blood pressure measurements.

In an Example 13, the method of any one of Examples 8-12, wherein the physiologic measurements include at least one of blood temperature and oxygen saturation measurements.

In an Example 14, the method of Example 12, wherein the sensors perform the blood pressure measurements in the left and right atria.

In an Example 15, the method of any of Examples 8-14, further comprising: displaying, based on the determination of how the first and second sets of physiologic measurements are trending, an instruction on what recommended medication(s) to administer and the dosage thereof.

In an Example 16, a method of informing changes to the pharmacologic management of a patient comprising: obtaining first measurement data based on a first set of hemodynamic measurements representing the right side filling pressure of the heart of the patient, wherein the first measurement data is transmitted from an implanted measurement system; obtaining second measurement data based on a second set of hemodynamic measurements representing the left side filling pressure of the heart of the patient, wherein the second measurement data is transmitted from an implanted measurement system; and determining, based on the first and second measurement data, whether each of the first and second sets of physiologic measurements is: trending lower or higher.

In an Example 17, the method of Example 16, wherein the patient is suffering from heart failure, kidney failure, or both.

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 8 is a close-up view of a measurement device according to some embodiments;

FIG. 9 is a cross-sectional diagram of the content of right atrium electronics in the measurement device of FIG. 8;

FIG. 10 is a cross-sectional diagram of the content of left atrium electronics in the measurement device of FIG. 8;

DETAILED DESCRIPTION

Definitions and Terminology

Figure 1A:
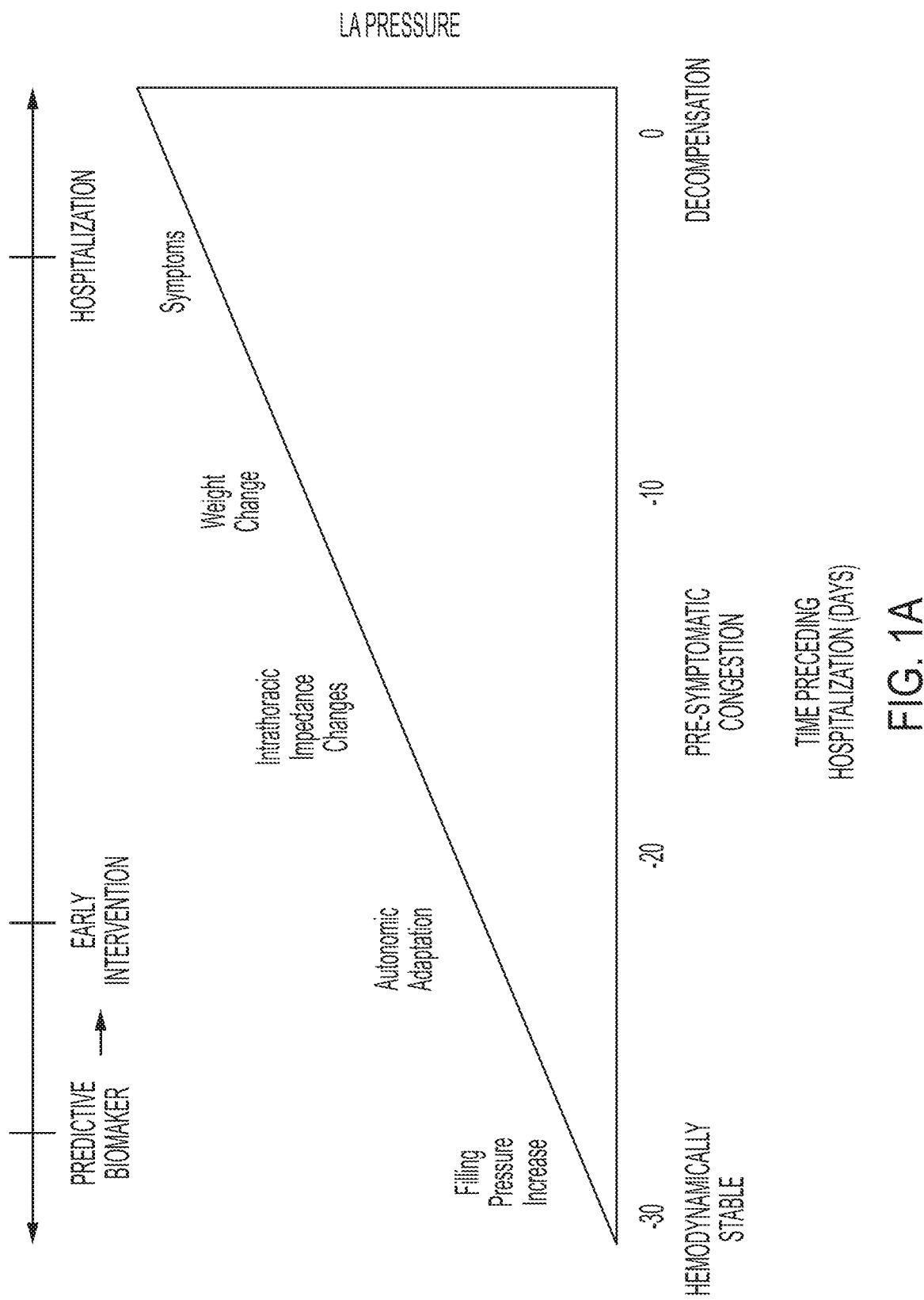
FIG. 1A is a chronological diagram illustrating symptoms and measurement methods of cardiac health of a patient during different stages preceding a possible rehospitalization event.
Figure 1B:
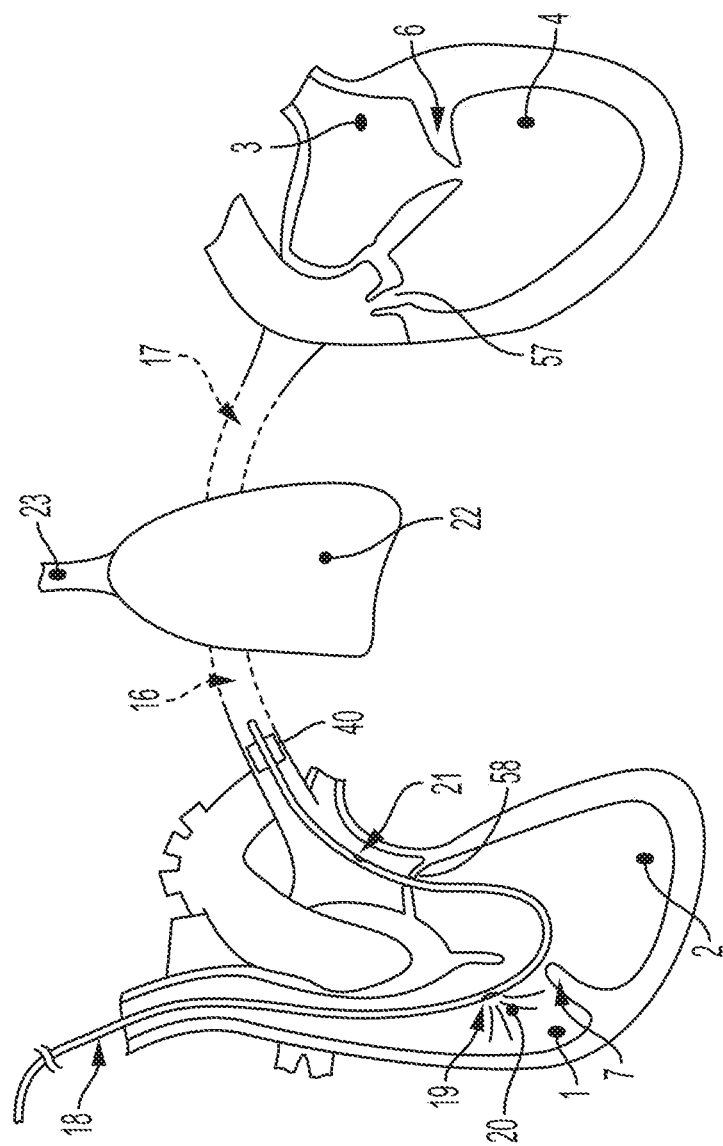
FIG. 1B is a schematic diagram of a heart and a lung of a patient using the prior-art measurement device (Swan Ganz right heart catheter) as discussed herein.

This disclosure is not meant to be read in a restrictive manner. For example, the terminology used in the application should be read broadly in the context of the meaning those in the field would attribute such terminology.

As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first.

DESCRIPTION OF VARIOUS EMBODIMENTS

Various aspects of the present disclosure are directed toward implantable medical devices such as device for performing physiologic measurements in the left and right sides of the heart. In certain instances, the various aspects of the present disclosure relate to methods and devices for performing pressure measurements. Additionally, the present disclosure also include a medical treatment system for determining administration of medications to a patient based on the measurements performed.

In prior-art measurement devices, surrogate measurement is chosen instead of directly measuring the left ventricle because of the risks associated with implanting measurement sensors within the left side of the heart. The left side of the heart takes oxygenated blood from the lungs and distributes it to the rest of the body, while the right side of the heart carries deoxygenated blood from the body to the lungs. When a sensor is implanted within the heart, a blood clot may form on the surface of the implanted sensor. The blood clot formed inside a blood vessel is called a thrombus. Occasionally, the thrombus may break off and travel to a different part of the body. When the thrombus lodges in a blood vessel that is too small to let it pass and blocks the blood flow therein, the lodged thrombus is called an embolus. The damage done by the embolus varies depending on its location. If the sensor is in the right side of the heart, the embolus would likely travel to the lungs, but if the sensor is in the left side, the embolus could travel to any part of the body. Among the worst-case scenarios in this situation is when the embolus lodges in an artery leading to the brain and blocks the blood flow, causing atherothrombotic stroke. Furthermore, none of the prior-art devices described above appear capable of simultaneously measuring pressure in two different portions of the heart, instead only measuring the pressure in the single region in which the measurement device is implemented. As such, there has been a need for a safer but more accurate measurement device.

Figure 2:
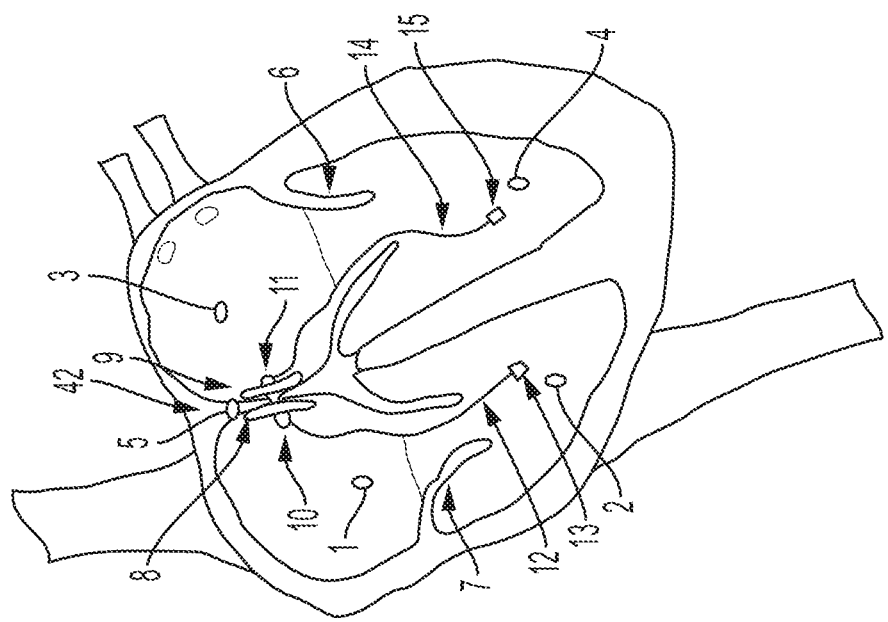
FIG. 2 is a cross-sectional diagram of a heart which uses a measurement device according to some embodiments.

FIG. 2 shows an embodiment of a measurement device 41 according to the present disclosure. The measurement device has a right side sensing element 10 and a left side sensing element 11, both of which sense and measure the pressure level within the respective side in which they are integrated. For example, in this example, the right side sensing element 10 measures the pressure level in the right atrium 1, while the left side sensing element 11 measures the pressure level in the left atrium 3 of the patient's heart. The pressure sensing elements 10,11, may incorporate MEMS technology or other pressure measurement means, as suitable, to measure intracardiac pressure levels.

As shown, the measurement device 41 has a right anchoring disc 8 and a left anchoring disc 9 which work together to help hold the measurement device 41 in place. As shown in the figure, the two discs 8,9 are designed to sandwich the atrial septum 5 between the two atria 1,3 (e.g., either actively engaging or contacting each side in an opposing manner). The placement of the measurement device 41 can be achieved with a catheter procedure and septal puncture. The sensing elements 10, 11 may be utilized along with a variety of devices that anchor to and extend across the atrial septum. Suitable examples may be found in a variety of Applicant's patent disclosures, including U.S. Pat. No. 9,949,728, "Septal closure device with centering mechanism"; US20170042705 "Implantable Product with Improved Aqueous Interface Characteristics and Method for Making and Using the Same"; U.S. Pat. No. 9,861,346 "Patent foramen ovale (PFO) closure device with linearly elongating petals"; U.S. Pat. No. 9,636,094 "Sealing device and delivery system"; and US20170105711, "Sealing Device and Delivery System."

In the example of FIG. 2, the measurement device 41 leaves no hole after surgery because of the anchoring discs 8,9 acting as occluders. The measurement device 41 can be configured to promote tissue ingrowth (e.g., into the anchoring discs 8,9) for any of a variety of reasons, including better tissue integration, reduced erosion, reduced thrombosis, or other beneficial features. Reduction of thrombosis can be particularly important on the left side of the heart. In some configurations, the measurement device 41 is configured such that the left side sensing element 11 is relatively low profile (e.g., relatively flat in profile). A relatively low profile may assist with reducing the potential for thrombosis. In some examples, some level of tissue overgrowth over the sensor may also be permitted while still permitting proper functioning of the left side sensing element 11. For example, the pressure on the left side (e.g., left atrium) may be read through a relatively thin layer of tissue, if necessary.

Figure 3:
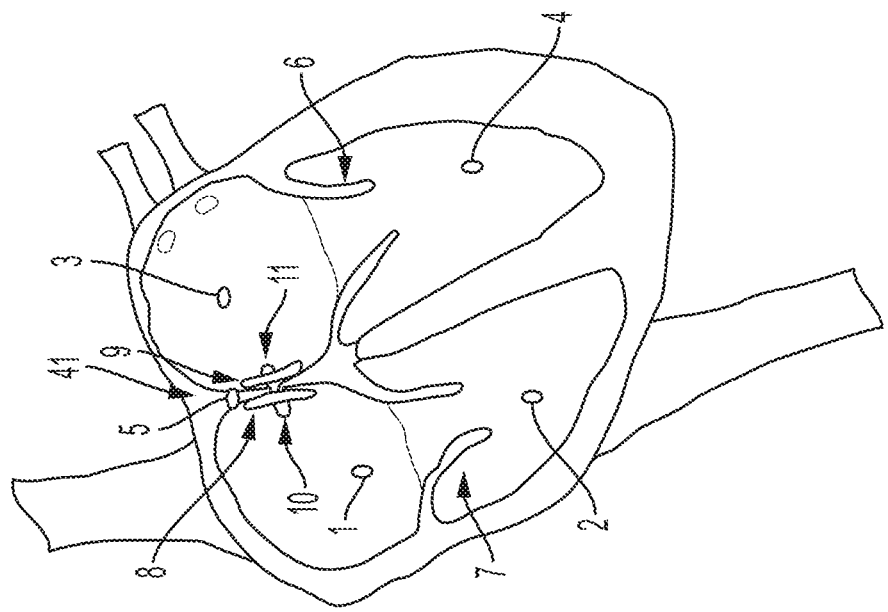
FIG. 3 is a cross-sectional diagram of a heart which uses a measurement device according to some embodiments.

FIG. 3 shows another embodiment of a measurement device 42 according to the present disclosure. In addition to the anchoring discs 8,9 and sensing elements 10,11 shown in FIG. 2, there are also sensing tethers 12,14 extending into the respective ventricles. Specifically, a right ventricle sensing tether 12 extends from the right side of the measurement device 42 (e.g., from the right side sensing element 10), into the right ventricle. A remote right ventricle sensing element 13 may be attached to the right ventricle wall (e.g., using soft tissue anchors and/or tissue ingrowth features). The remote right ventricle sensing element 13 is configured to measure the pressure inside the right ventricle.

Similarly, a left ventricle sensing tether 14 extends from the left side of the measurement device 42 (e.g., from the left side sensing element 11) into the left ventricle. A remote left ventricle sensing element 15 may be attached to the left ventricle wall (e.g., using soft tissue anchors and/or tissue ingrowth features). The remote left ventricle sensing element 15 is configured to measure the pressure inside the left ventricle.

Figure 4:
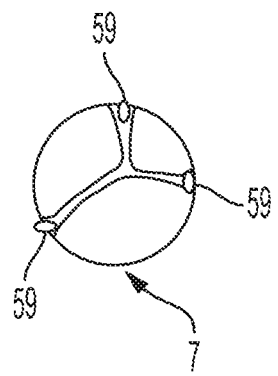
FIG. 4 is a cross-sectional diagram of the commissures of a tricuspid valve.
Figure 5:
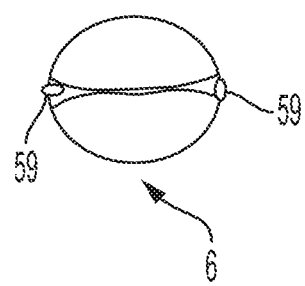
FIG. 5 is a cross-sectional diagram of the commissures of a mitral valve.

The remote sensing elements 13,15 are configured to measure pressures in different portions of the heart than the sensing elements 10,11. In at least this manner, the measurement device 42 is configured to provide additional measurement data (e.g., left ventricular and right ventricular pressure data) for analysis. The sensing tethers 12, 14 may be arranged or otherwise positioned to extend through the commissures of the valves that reside between the right atrium and the right ventricle (tricuspid valve) and the left atrium and left ventricle (mitral valve). FIGS. 4 and 5 show optional positions for the sensing tethers 12, 14, which include positions adjacent the commissures 59 located between the leaflets of the tricuspid valve 7 (FIG. 4) or the mitral valve 6 (FIG. 5) through which the sensing tethers 12,14 extend to reach their respective ventricles. In various examples, by positioning the tethers 12, 14 adjacent the commissures 59 the impact of the tethers on valve function and/or likelihood of thrombosis may be reduced.

In one example, additional sensors may be incorporated into the sensing tethers 12,14. In another example, the additional sensors may be implemented into other elements of the measurement device 42 at the points of tether attachment to measure a force, i.e. tensile stress, on the tethers 12,14. The force on the tethers 12,14 may be used as an indication of local blood flow velocity within the heart, and this measurement data may be used by itself or in combination with other measurement parameters to assess cardiac function of the patient. Advantages of measuring such force on the tethers 12,14 including the ability to obtain data which serves as indicators relating to the cardiac function such as mitral inflow velocity, tricuspid flow, and severity of a potential regurgitation, for example, which may be difficult to detect using other means of measurement. To accurately measure this force, the tethers 12,14 and remote sensing elements 13,15 in this example are at least partially free-floating (i.e. not attached to the walls of an atrium or ventricle). In addition to, or as an alternative to measuring pressure and/or force, the various sensing elements may be configured to measure temperature (e.g., by including one or more thermistor elements). By including temperature sensing capabilities, a cold bolus (e.g., fluid) may be introduced into the cardiac system and the rate of temperature equalization may be used to determine cardiac output at various locations in the heart. In contrast to methods that utilize a cold fluid bolus, various examples include use of a cold air bolus in the lungs to measure the rate at which temperature equalizes from blood returning from the lungs.

Figure 6:
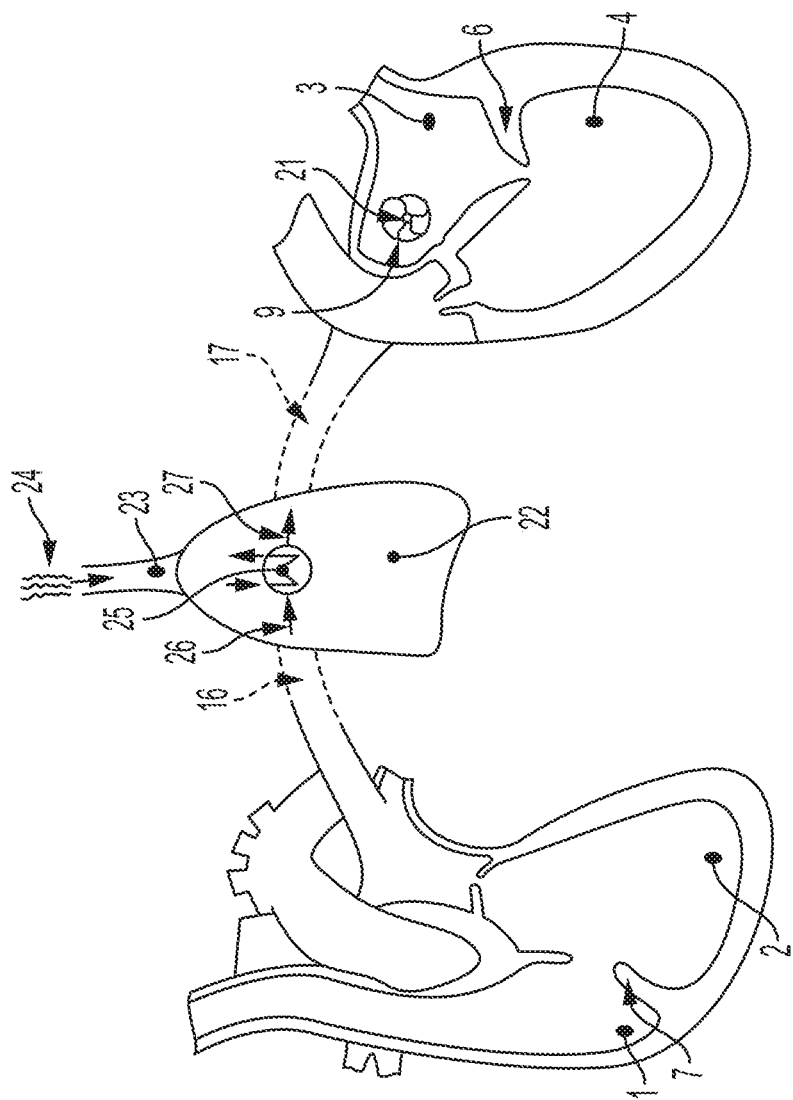
FIG. 6 is a schematic diagram of a heart and a lung of a patient using a measurement device according to some embodiments.

FIG. 6 shows how a cardiac output is affected by and therefore can be measured via thermodilution with a cold air bolus and a left atrium sensor, or thermistor 21, according to some embodiments. Initially, cold air bolus 24 is injected into the lung 22 (e.g., by introducing inhalation of a bolus of cold air into the lungs through the patient's trachea 23). Then, heat exchange 25 takes place when warmer deoxygenated blood 26 enters the lung through the pulmonary artery 16 and is then cooled by the cold air bolus 24 during oxygenation. Afterwards, cooler oxygenated blood 27 leaves the lung through the pulmonary vein 17 into the left atrium 3 where the thermistor 21, immobilized using the left anchoring disc 9, measures the temperature in the left atrium 3. If more blood is flowing, the temperature within the left atrium 3 would return to normal temperature sooner than when less blood is flowing. As such, the inhalation of cold air in this case can be used to determine the initial drop in the blood temperature in the left atrium 3, which is used to correlate the time for the temperature to return to normal. The rate at which the temperature returns to normal correlates with the cardiac output.

Figure 7:
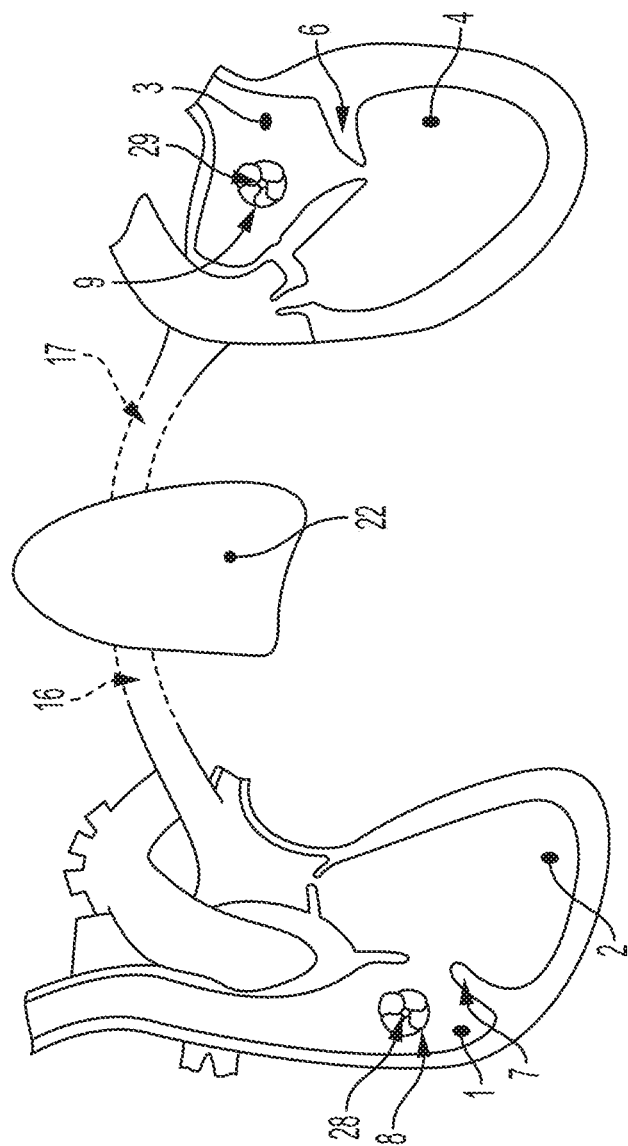
FIG. 7 is a schematic diagram of a heart and a lung of a patient using another measurement device according to some embodiments.

As a further additional or alternative feature, one or more O2 sensors may be included at one or more of the first pair of sensing elements 10,11 and the remote second pair of sensing elements 13,15. FIG. 7 shows a diagram of blood flow from the right to left side of the heart through a lung and can be used to describe how cardiac output can be measured via O2 blood saturation sensors 28,29 (e.g., using Fick's Law). According to various examples, a right O2 saturation sensor 28 is placed in the right atrium 1 (e.g., associated with the sensing element 10 immobilized using the right anchoring disc 8), and a left O2 saturation sensor 29 is placed in the left atrium 3 (e.g., associated with the sensing element 11 immobilized using the left anchoring disc 9), to measure the SvO2 and SaO2 levels in their respective areas of measurement.

Fick's Law dictates that the blood flow to the patient's heart can be calculated using a marker substance, which in this case is oxygen (O2). The necessary data for making such calculations include the amount of oxygen taken up by the heart per unit time, the O2 blood saturation in the pulmonary artery, and the O2 blood saturation in the pulmonary vein. In this case, the O2 blood saturation of the pulmonary artery 16 is measured at the right atrium 1, and the O2 blood saturation of the pulmonary vein 17 is measured at the left atrium 3. Other data for the calculation can include maximal oxygen uptake (VO2 max), which is the maximum rate of oxygen consumption measured during incremental exercise, and hemoglobin test, which in combination with the arterial and venous percentages will determine oxygen concentration.

As explained above, different sensors can be implemented in the embodiments as disclosed herein (e.g., pressure, flow, temperature, and/or O2), with each measurement contributing vital data regarding the health of the patient's heart. The sensors themselves can be of various shapes and sizes, as deemed suitable by a person of ordinary skills in the art, to be implemented inside a patient's heart.

FIGS. 8-10 show additional details of possible sensor element configurations. As shown in FIG. 8, a measurement device 43 has a right atrium sensing element 30 included in right atrium electronics 37 and a left atrium sensing element 31 included in left atrium electronics 38. The electronics 37,38 are attached to their respective anchoring discs 8,9 as shown in FIG. 8. FIG. 9 shows that the electronics 37,38 both include a control module 33 (e.g., printed circuit board) in a proximal part 34 of a case 36 with regard to the anchoring discs 8,9. The case 36 may be made of titanium, stainless steel, or other suitable materials. The right atrium electronics 37 further include the right atrium sensing element 30 and an antenna coil 35. The left atrium electronics 38 further include the left atrium sensing element 31 and a power source 32 (e.g., battery and/or inductive power source). In this configuration, an external reader device, such as the external charger and communications relay 70 in FIG. 18, charges the power source 32 as well as communicating with the electronics 37,38 to obtain the measurement data stored in a memory implemented in the control modules 33.

The control modules 33 can be designed such that they are configured to perform a sequence of steps for taking measurements within different portions of the heart (e.g., each of the chambers), whether the measurements are in blood pressure, temperature, and/or oxygen saturation), as well as to store the data until the external reader device can access the data, usually wirelessly. Furthermore, the power source 32 can be any suitable power source that can be used in this implementation. For example, the power source can be coupled to a charging coil which enables inductive charging of the power source such that the external reader device can remotely charge the power source from outside the patient's body, which reduces the need to exchange the power source once it runs out of power. For example, the antenna coil 35 can be used as a charging coil in addition to performing relay/communication functions.

Figure 13:
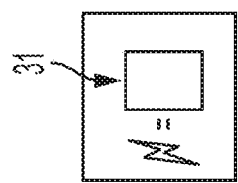
FIG. 13 is a cross-sectional diagram of the contents of left atrium electronics in the measurement device of FIG. 11.
Figure 12:
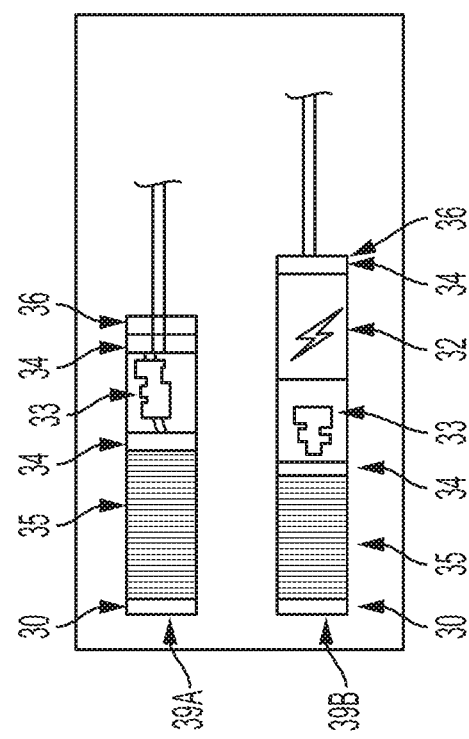
FIG. 12 is a cross-sectional diagram of two examples of the contents of right atrium electronics in the measurement device of FIG. 11.
Figure 11:
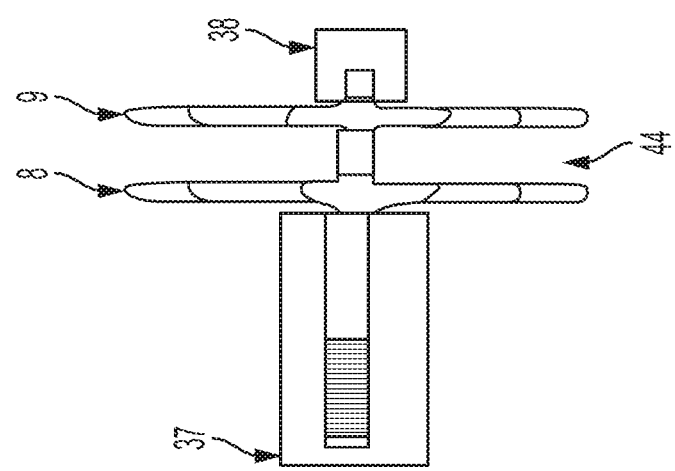
FIG. 11 is a close-up view of a measurement device according to some embodiments.

FIGS. 11-13 show various configurations that may be used in various examples. As shown, the left atrium electronics 38 of a measurement device 44 only include the left atrium sensing element 31 (e.g., sensing, temperature and/or O2). Minimizing the number of components/elements on the left side of the device may help minimize the overall size of the device and the associated amount of foreign material in the left atrium. As described above, this may reduce the potential for thrombosis and foreign body response. As such, in various examples (e.g., as shown in inset view of the configuration 39B), the right atrium electronics 37 include the power source 32 to power the sensing elements 31, any associated data storage elements, and more generally the control module 33. In another example as shown in configuration 39A of the inset view of FIG. 12, the right atrium electronics 37 do not include an onboard power source. In such embodiments, measurement data may only be taken when an external reader device is engaged to power the measurement device 44 (e.g., using inductive power to activate the sensing elements 30,31 and control module 33).

Figure 15:
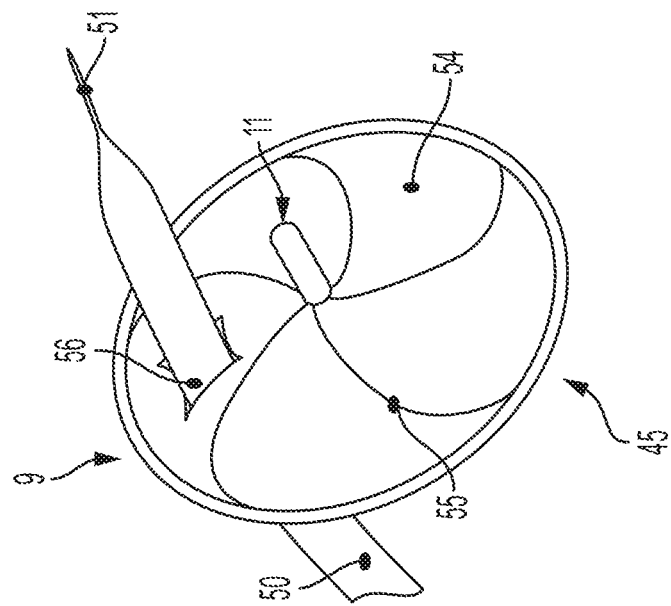
FIG. 15 is a close-up view of the measurement device of FIG. 14 being punctured.
Figure 14:
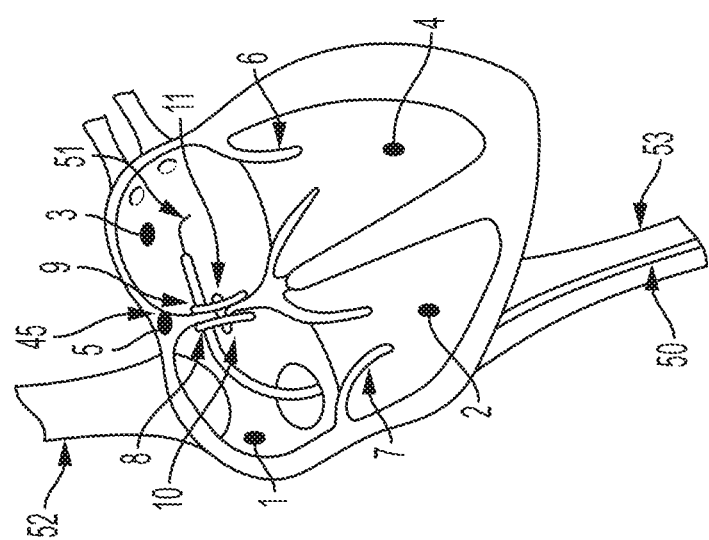
FIG. 14 is a cross-sectional diagram of a heart which uses a measurement device according to some embodiments, where a portion of the measurement device is punctured by a trans-septal needle.

In various examples, one or more of the measurement devices 41,42,43,44 (e.g., one or both of the anchoring discs 8,9) is configured to be fenestrated, or crossed by a surgical implement (e.g., trans-septal needle) following implantation. FIGS. 14 and 15 show a puncture needle 51 attached to the end of a catheter sheath 50 penetrating the surfaces of the anchoring discs 8,9 to indicate that the measurement device 45 is re-crossable (e.g., may be penetrable by a needle and followed by a sheath).

During certain procedures or operations, it may be imperative to enter the left atrium 3 even though the measurement device 45 has been implemented in the atrial septum 5 between the atria 1,3. In such case, the measurement device 45 is configured to have re-crossable surfaces in the anchoring discs 8,9 so that the puncture needle 51 can penetrate these surfaces to perform the procedures. FIG. 14 shows the needle 51 and catheter sheath 50 entering the right atrium 1 from the inferior vena cava 53, but in some instances may enter the right atrium 1 from the superior vena cava 52 as necessary. In this embodiment, the surface of the anchoring discs 8,9 includes a material than can be safely penetrated, such as an expanded polytetrafluoroethylene (ePTFE) membrane 54, although other suitable materials can be implemented to provide re-crossing capability. The outer edge of the anchoring disc 9 is defined by a nitinol frame 55 which also extends radially from the left side sensing element 11 to the outer edge, although other suitable materials may be used for the frame as well. The needle 51 forms a puncture hole 56 in the membrane 54 to allow for the catheter sheath 50 to pass through.

Figure 16:
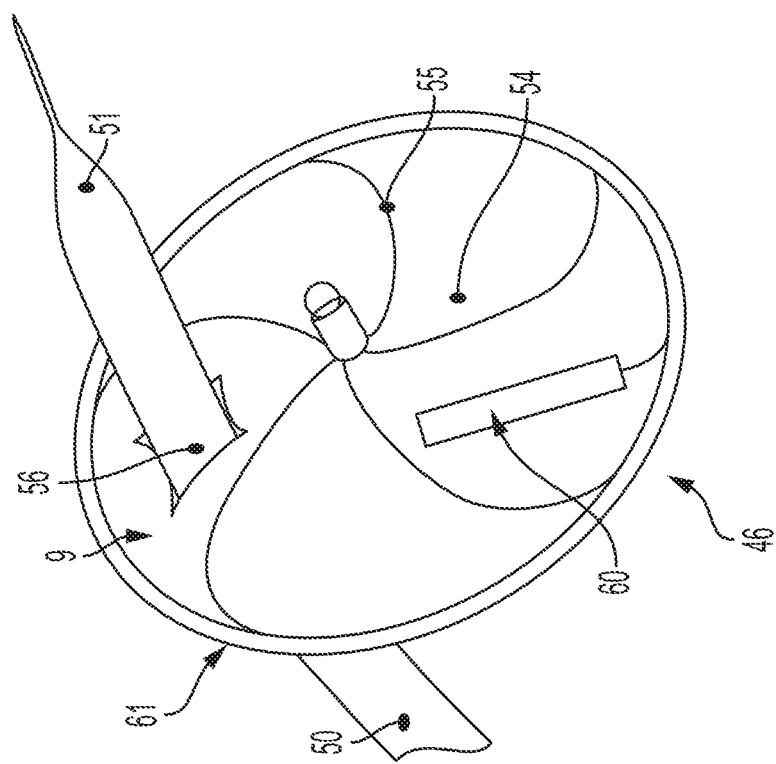
FIG. 16 is a close-up view of another measurement device according to some embodiments, where a portion of the measurement device is punctured by a trans-septal needle.

FIG. 16 shows another embodiment as disclosed herein where the left side sensing element 60 of a measurement device 46 is located on a portion of the left anchoring disc 9. For example, the left side sensing element 60 may be located on membrane material (e.g., ePTFE membrane 54) of the left anchoring disc 9, as opposed to the frame of the left anchoring disc 9 (e.g., center eyelet or outer frame). In this embodiment, the left side sensing element 60 is coupled to the membrane 54 to help prevent the sensing element 60 from protruding outward from the septal wall, or reduce the amount the left sensing element 60 protrudes from the septal wall from the measurement device 46. In this embodiment, an antenna coil 61 is implemented in the anchoring disc 9. As shown, the sensing element 60 is attached to the antenna coil 61, and the antenna coil 61 is wrapped around the ePTFE membrane 54 to form the outer edge of the left anchoring disc 9, thereby defining the periphery of the left anchoring disc 9. Additional embodiments may further reduce the amount the left sensing element 60 protrudes from the septal wall. For example, in one embodiment, the left anchoring disc 9 may be replaced with a small tissue anchoring structure which help align the outer surface of the left sensing element 60 to be substantially flush with the surface of the surrounding septal wall, such that the sensing element 60 would not visibly protrude from the septal wall. For example, small hooks or other suitable structures may be implemented to hold the left sensing element 60 in place. In another embodiment, a cover or other similar component may be employed over the left sensing element 60 to prevent the sensing element from substantially protruding into the left atrium. The cover may be made of a material that is chemically inert such as low temperature isotropic (LTI) carbon and diamond like carbon (DLC), or polymers such as polytetrafluoroethylene (PTFE), expanded PTFE, or polyethylene terephthalate (PET). In some examples, the cover may be a thin film placed over the left sensing element 60 to promote tissue ingrowth over the sensing element.

Figure 17:
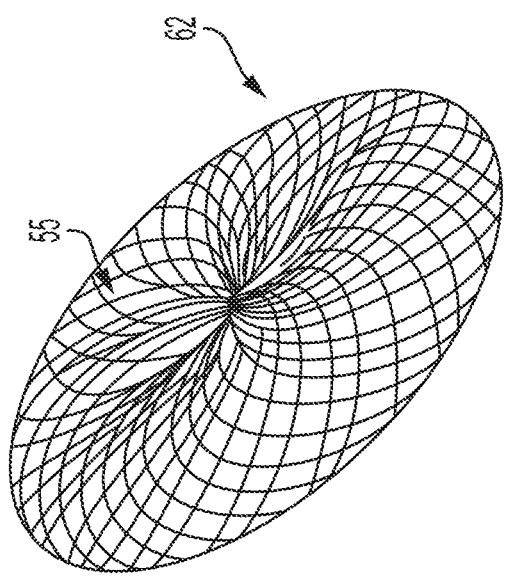
FIG. 17 is a close-up view of a mesh configuration used in a measurement device according to some embodiments.

FIG. 17 shows another potential configuration for the medical device 46 where the left anchoring disc 62 uses a frame (e.g., nitinol) configured into a mesh design that defines the left and/or right disc(s). The configuration of FIG. 17 may or may not employ a cover or membrane 54 (e.g., ePTFE). The re-crossable surface is designed such that catheters with a French gauge suitable to fit between the frame elements (e.g., up to 24 Fr) may fit through the anchoring disc(s) without interfering with the electronics. Also, it should be appreciated that although the anchoring discs illustrated in the figures are relatively flat and circular in structure, any of the anchoring disc configurations described herein can use other shapes (e.g., rectangular, triangular, etc.) as well. Moreover, the anchoring discs may be configured with a curved side profile (e.g., concave and/or convex) to accommodate for the different contours defining the surface within the heart to which the anchoring discs are to be engaged.

In one embodiment, the measurement device 45,46 can also act as a therapeutic device, such as an intra-atrial shunt, a controllable intra-atrial shunt, an occluder for atrial septal defects (ADS), and so on. The measurement device 45,46 can act as such a controllable shunt because it is located at an interatrial septum between the left and right atria, and the membrane 54 can be opened via interventional or noninvasive procedures. As such, the membrane 54 may be expanded, contracted, opened, closed, fenestrated, sealed, punctured, resealed, traversed, or crossed using appropriate tools during different procedures to actuate the controllable shunt. The use of a needle to make a puncture hole 56 in the membrane 54 as discussed above is one example of the interventional procedure. Other interventional procedures include mechanical, thermal, laser, ultrasound, and inductive methods. On the other hand, the opening of the hole can be triggered via wireless, extracorporeal energization, including inductive energy transfer and ultrasound energy transfer. In one embodiment, the membrane 54 can be melted to form an opening after exposing the membrane 54 to thermal or ultrasound energy, i.e. via thermal activation. An advantage in having an opening in the membrane 54 includes, when the measurement device 45,46 is located between the left and right atria, reducing the left atrial pressure when it rises to a life-threatening level. One advantage in this configuration is that even after the opening is formed, the measurement device 45,46 can continue taking measurements within the two atria. The size of the shunt can be adjusted based on the required degree of pressure relief. For example, if the pressure is significantly higher than the normal level such that the pressure must be lowered immediately, the shunt can be opened wider. When the shunt is opened via mechanical piercing or thermal ablation, it can prevent embolization as well. Furthermore, a pressure-sensitive valve may be implemented in the measurement device 45,46 such that the membrane 54 opens to form the shunt above a threshold pressure level. In another example, the valve may also track and transmit its status (i.e. whether the shunt is open or closed in the valve, as well as the degree of opening in the shunt) which may serve as an indication of a pressure differential within the heart. Therefore, a remote monitoring system (for example a remote device 72 in FIG. 18) which receives data from the valve can use the status data of the valve to determine a difference in pressure between the left and right atria.

Figure 18:
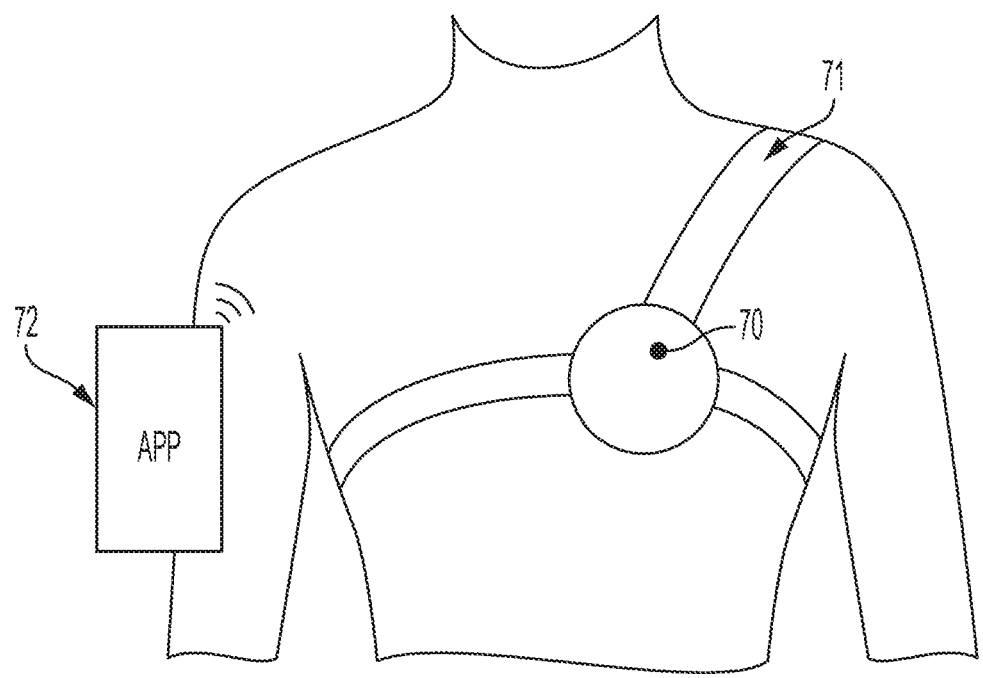
FIG. 18 is a schematic diagram of a wearable harness for an external reader device for a measurement device according to some embodiments.

FIG. 18 shows an example of external charging and communications relay according to some examples. As shown, the external charger and communications relay 70 is a device which can charge or power a power source of the measurement device (for example, the battery 32 in the measurement devices 43,44) via electromagnetic induction, as well as to communicate with the measurement device 43 or 44 to obtain the measurement data. The external charger and communications relay 70 may be worn (e.g., using a harness 71) such that the location of the charger and relay 70 is placed at an operable location for the charger and relay 70 to charge and obtain data from the measurement device. A monitoring system 72, which can be a smart device such as a smartphone, can be used by the patient or other party (e.g., medical service provider or remote monitoring facility) to receive information regarding the measurement data via an application software in the monitoring system. For example, the remote device 72 can visually show the blood pressure, temperature, and/or oxygen saturation in a simple, user-friendly interface. If the patient is visually impaired or prefers audio notifications, the remote device 72 can provide audio output to alert the patient if the sensor measurements indicate that the patient's heart may be at risk of acute decompensation episodes, so that the patient can go to a hospital for a further examination. The remote device 72 can also upload the measurement data onto a server (not shown) to be collected by medical service providers or a database to remotely monitor the conditions of the patient's heart.

Based at least upon the foregoing, it should be appreciated that a variety of sensor locations are contemplated and may be implemented in any combination.

For example, to measure the left ventricular pressure, a tethered sensor can be sent off the left anchoring disc, between the mitral valve leaflets, and into the left ventricle, where tissue ingrowth can implement the sensor into the wall of the left ventricle. The sensor directly measures the left ventricular systolic and diastolic pressure, which also gives a direct indication of systolic systemic blood pressure To measure the aortic pressure, the tethered sensor can be sent off the left anchoring disc, between the mitral valve leaflets, through the aortic valve, and into the aorta, where the sensor is secured to the wall of the aorta. This placement allows for direct measurement of the aortic pressure which gives a direct indication of systolic and diastolic blood pressures.

To measure the right ventricular pressure, the tethered sensor can be sent off the right anchoring disc, between the tricuspid valve leaflets, and into the right ventricle, where tissue ingrowth can implement the sensor into the wall of the right ventricle. The sensor directly measures the right ventricular pressure which gives a direct indication of systolic and diastolic right ventricular pressures.

To measure the pulmonary artery pressure, the tethered sensor can be sent off the right anchoring disc, between the tricuspid valve leaflets, through the pulmonary valve, and into the pulmonary artery, where it is secured. This placement allows for direct measurement of the pulmonary pressure which gives a direct indication of pulmonary status via pulmonary systolic and diastolic pressures.

Furthermore, the implanted device that measures the left and right atrial pressures can be used in combination with other medical devices. Examples of such medical devices include, but are not limited to, blood pressure cuffs, pulse-oximeters, scales, creatinine testing devices, smart devices, and wearable medical tracking devices, to name a few. The measurement device 41 can also be combined with other implantable devices, such as a ventricular assist device (VAD), drug delivery shunt or system, or other device. The measurement device 41 may provide feedback to the other implantable device(s), as part of a closed loop or open loop feedback system.

Figure 21:
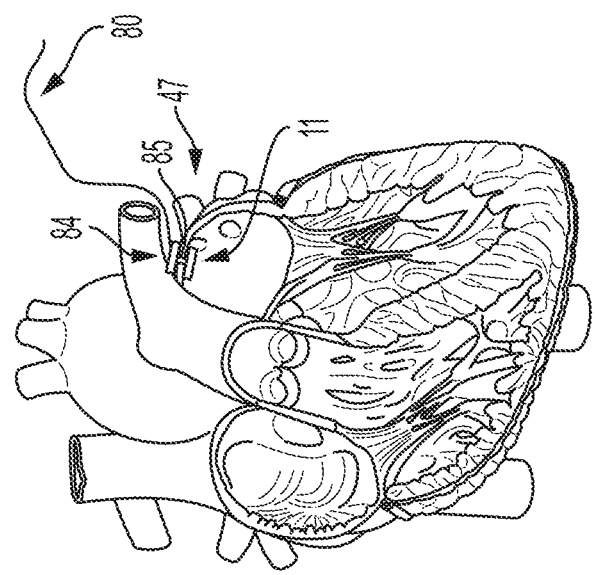
FIG. 21 is a cross-sectional view of a heart with the sensor implanted and immobilized using a pledget according to some embodiments.
Figure 20:
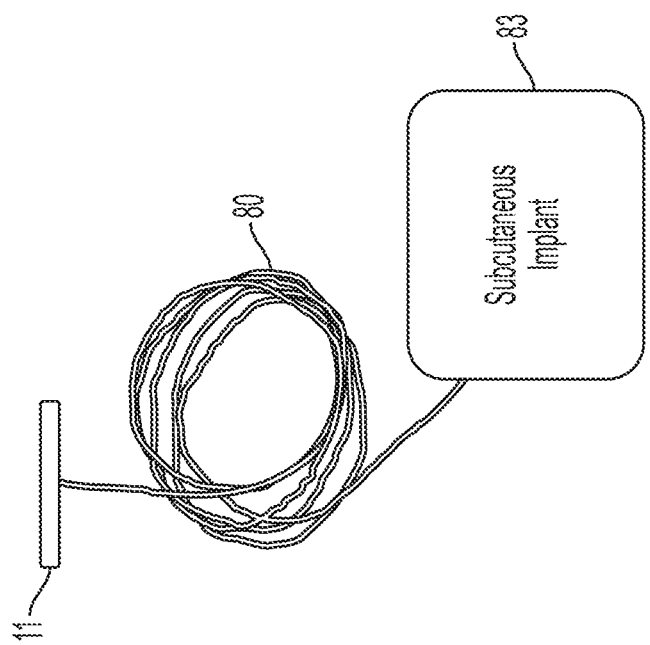
FIG. 20 is a schematic diagram of a sensor connected to a subcutaneous implant according to some embodiments.

FIGS. 19 to 22 show additional sensor element examples as well as the associated delivery systems and methods. As shown, the left side sensing element 11 may be coupled with a tether 80, with the sensor element 11 and tether 80 configured to delivered through a needle delivery system 81 shown schematically in FIG. 19. Generally, the delivery system 81 may include a catheter and associated delivery needle 82 at a distal end of the catheter that is used to access a target area in the body (e.g., via ultrasound, radiographic, optical or other guidance). For example, the needle may be used to puncture a wall of the heart (e.g., left atrial wall) and the left side sensing element 11 may be advanced through the needle 82 into the target space (e.g., the left atrium). The needle 82 may then be retracted and the sensing element 11 may be pulled or tensioned against an inner wall of the heart (e.g., the inner wall defining the left atrium). A pledget or other anchor 84 may be advanced (e.g., over the tether 80) to a position on an opposite side of the heart wall from the sensing element 11 (e.g., a location on an outer wall of the heart proximate to the location of the sensing element 11) to help secure the sensing element 11 in place (e.g., as shown in FIG. 21). The tether 80 may be connected to a subcutaneous implant 83 that handles power, signal processing, and data transmission functions as shown in FIG. 20.

The subcutaneous implant 83 can include a battery, an antenna, and a control module (e.g., a microchip) to help control data collection and communication functions. In one example, the measurement device 47 may include a plug 85 that is placed between the sensing element 11 and the pledget 84 to help fill the fenestration left by the needle 82.

Figure 22:
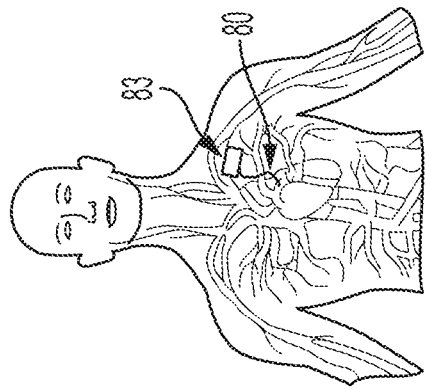
FIG. 22 illustrates one example of a location of the subcutaneous implant in the patient's body according to some embodiments.
Figure 19:
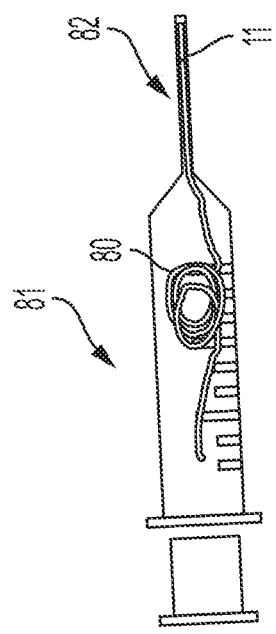
FIG. 19 is a schematic diagram of a syringe or catheter with a needle containing a sensor tethered to a wire according to some embodiments.

FIG. 22 shows a subcutaneous implant 83 on the other end of the tether 80 opposite from the sensing element 11. Multiple sensor elements similar to the left side sensing element 11 can be placed in any different parts of the heart as deemed suitable by the medical service providers. For example, after the left side sensing element 11 is placed in the left atrium, another sensing element such as the right side sensing element 10 can be implemented into the right atrium using the same technique that is used to place the sensing element 11 in the left atrium. Another similar sensing element can be implanted in the left ventricle, right ventricle, or any other location in the heart or vasculature as desired. As such, any number of sensor elements can be implemented by penetrating a wall of the heart to take measurements (pressure, temperature and/or oxygen saturation) in any of the chambers of the heart or associated vasculature.

The tether(s) associated with the sensor elements can be coupled to the same subcutaneous implant or different subcutaneous implants as desired. Whether a single subcutaneous implant with data receiving and communication capabilities or different subcutaneous implants, it should be understood that any of the combination of measurements (pressure, temperature and/or oxygen saturation) at any combination of locations (e.g., left atrium, right atrium, left ventricle, and/or right ventricle) may be realized using the tethered sensor elements described in association with FIGS. 19 to 22.

The pressure measurement data obtained using the sensing elements 10,11,13,15 as described herein can be used to perform pulse-contour method, which is another method that is used to measure the cardiac output of the patient. This method uses the continuous pressure measurement data to plot a pressure-versus-time graph for the patient's heart, after which the pressure integral, i.e. the area beneath the plotted line on the pressure-versus-time graph, is used to determine the stroke volume (SV) of the portion of the heart that is being measured. The value of SV multiplied by the heart rate is the cardiac output.

Figure 23:
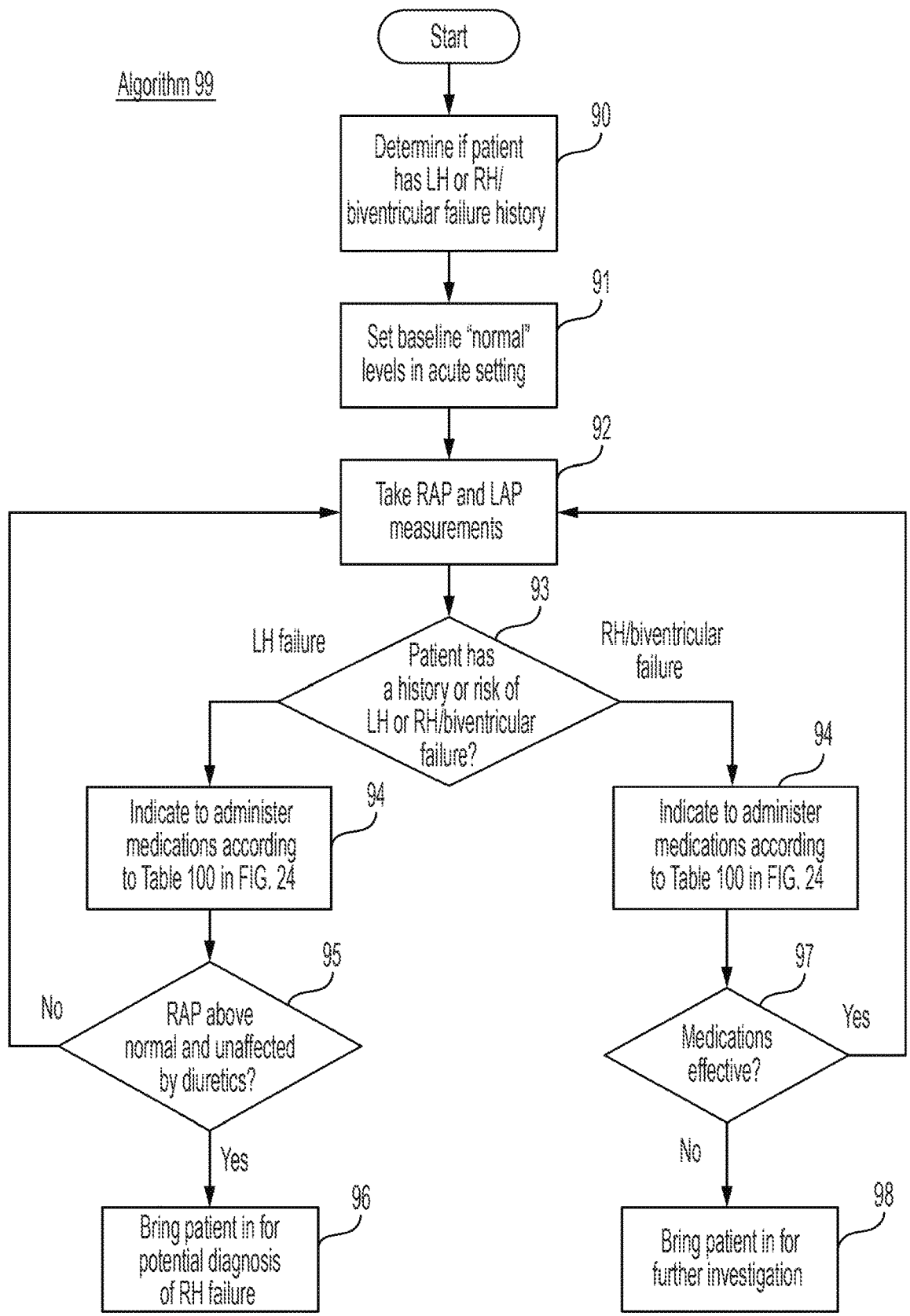
FIG. 23 illustrates a block diagram of a method to determine actions that need to be taken based on pressure measurements according to some embodiments.

FIG. 23 is a flow chart showing a remote medical treatment monitoring method 99 that can be implemented using one or more electronic devices, such as the monitoring system 72, using measurement data received from the measurement device 41, for example, or any of the sensor elements described herein. In some examples, the method 99 is used for patients with a history of left heart failure, to determine treatment protocols guided by measured right and left heart physiologic metrics (e.g., pressure, temperature, and/or oxygen saturation).

Regardless, in some embodiments, in an optional first step 90 the service provider determines if the patient receiving treatment has a history of either left heart (LH) or right heart (RH)/biventricular failure. The method 99 may be used for patients with a risk of LH or RH/biventricular failure as determined by the medical service providers, regardless of history. In optional step 91, the medical service provider set a baseline "normal" level for applicable physiologic metrices (e.g., the left and right atrial pressures) in the acute setting by performing various tests on the patient to determine, based on the current condition of the patient, what normal levels (pressure, cardiac output, and/or oxygen saturation) would be. Baseline values can then be entered into the system which transfers the data to the monitoring system 72. In the example illustrated in this figure, the pressures being measured are the left atrial pressure (LAP) and the right atrial pressure (RAP). Other embodiments may include other measurements of other parts of the heart, as deemed appropriate by the medical service provider.

In some examples, the monitoring system 72 receives RAP and LAP measurements from the sensors in step 92, such as the right side sensing element 10 and the left side sensing element 11. In one implementation, the measurements include whether the pressure values of the right atrium and the left atrium are trending below, at, or above the normal level. In another example, the method may also consider whether the pressure values are increasing, decreasing, or staying steady as an additional input into the overall assessment.

Figure 24:
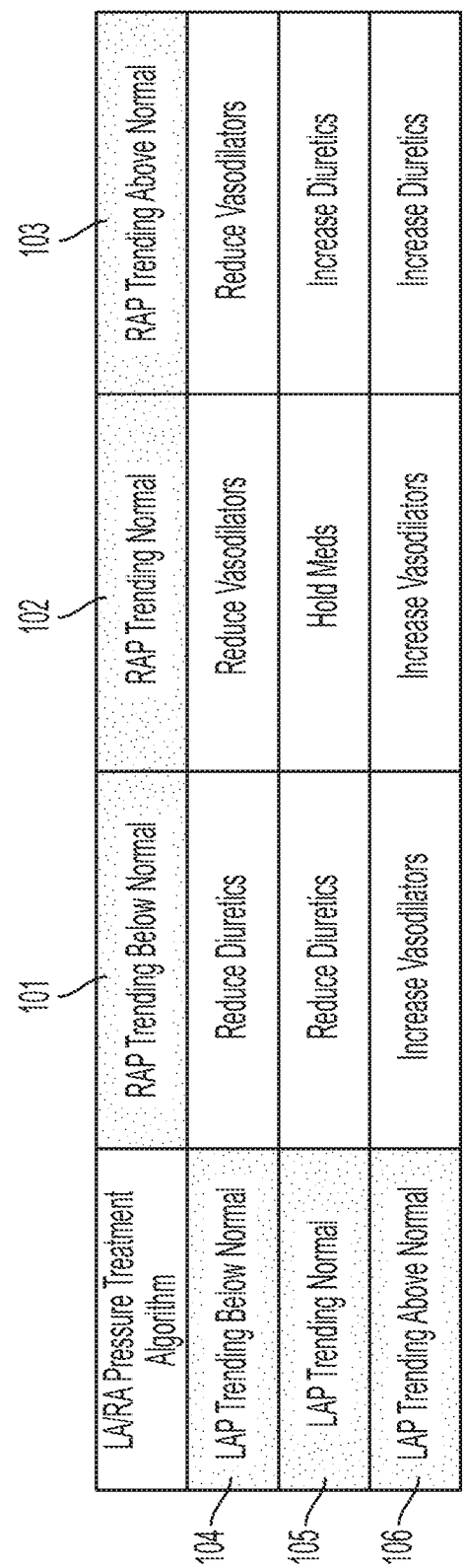
FIG. 24 illustrates a medication administration reference table using two sets of measurement data as implemented by the method in FIG. 23.

In optional step 93, the monitoring system 72 confirms whether the patient has a history of LH or RH/biventricular failure. The monitoring system 72 optionally uses a medication administration reference table 100 in FIG. 24 to determine and indicate if dosage of certain medications needs to be increased or reduced, in step 94. Alternatively, a medical service provider (e.g., physician) optionally uses the data directly to assess what treatment regimen (e.g., pharmacological) is appropriate based upon the data using the methodology of table 100.

As shown, the table 100 has three columns and three rows, where the columns pertain to "RAP trending below normal" 101, "RAP trending normal" 102, and "RAP trending above normal" 103, and the columns pertain to "LAP trending below normal" 104, "LAP trending normal" 105, and "LAP trending above normal" 106. For example, if the RAP is trending below normal but the LAP is trending above normal, the method would include the step of "Increase Vasodilators" according to the table 100. If automated, a consistent "message" or communication could be relayed to a user of the monitoring system. On the other hand, if the RAP is also trending above normal, the method would include the step of "Increase Diuretics". Again, if automated, a consistent "message" or communication could be relayed to a user of the monitoring system. It should be noted that when the LAP and RAP values are both in the normal level (i.e. the box defined by the "LAP normal" row and "RAP normal" column), one method would include not altering any medications.

After the initial medication is administered, the method 99 includes verifying to see if the RAP is still trending above normal and if the RAP value is unaffected by diuretics, in step 95. This may occur in the second example shown above, where the LAP and RAP are both trending above normal so the amount of diuretics administered to the patient is increased, but a subsequent measurement of the RAP shows that this pressure is still above normal. In this instance, the monitoring system 72 could display an indication in step 96 instructing the medical service provider to bring the patient in for a potential diagnosis of RH failure (or the medical service provider could carry out the step 96 based upon the data). Among other possible causes of high RAP is primary pulmonary arterial hypertension. When the medical service provider tests the patient for possible diagnosis of these conditions, the medical service provider can set a new baseline value range for the "RAP normal" level and update the patient's status as having a history of RH/biventricular failure so that moving forward, the method will proceed to step 97 instead of step 95 in the future. Otherwise, if the RAP decreases to the normal level, the monitoring system 72 optionally goes back to step 92 to take subsequent RAP and LAP measurements.

Returning to step 93, if the monitoring system 72 (or the medical service provider) confirms that the patient has a history of RH/biventricular failure, the method 99 proceeds to step 97 after determining which medication to increase or decrease based on analysis outlined in table 100. In step 97, the method 99 includes determining if the medication administered in step 94 is effective. For example, the method 99 may include comparing the previous LAP and RAP values with the new LAP and RAP values taken after the medication is administered. If the comparison shows that there is an insufficient change in the status in a way that indicates that the administered medication is ineffective (for example, if the LAP or RAP is still below normal and the medication is not causing it to increase toward normal level, or if the LAP or RAP is still above normal and the medication is not causing it to decrease toward normal level, etc.) the medical service provider may bring the patient in for adjusted treatment and/or the monitoring system 72 may provide a message or other communication indicating that further diagnosis/treatment is warranted in step 98. The possible lack of efficacy of the medications may be a sign of increased exigency or that immediate medical attention is otherwise warranted. Otherwise, if the administered medication is showing apparent efficacy in moving LAP and RAP toward nominal or desired levels, the method returns to step 92 and the monitoring system 72 continues to receive and evaluate new measurements for assessing patient health.

Use of at least two sets of measurement data (in this example, LAP and RAP measurements) in assessing cardiac function is advantageous over prior-art methods with only one set of measurement data for a variety of reasons, including that the second set helps facilitate more accurate root cause diagnosis and treatment.

In another embodiment, the method 99 may be programmed so that instead of using the actual measured LAP and RAP values, a ratio of LAP to RAP (or a ratio of RAP to LAP) may be used to determine which medications to administer and how much. This methodology may be based on the understanding that the pressures within the left and right atria should correspond to a desired ratio (e.g., 2:1 LAP:RAP) in a healthy heart, therefore the ideal ratio of LAP to RAP can be determined (e.g., an ideal ratio of 2:1 pressures are desired), and any ratio that is significantly smaller or larger than the desired ratio (e.g., 2:1) would pose a threat to the patient's health.

In some examples, if the ratio of LAP to RAP is above a threshold value (i.e. the LAP is much higher than the RAP) and keeps increasing in a patient with a history of LH failure, the method may include a determination that the amount of vasodilators being administered should be increased. The threshold ratio value of LAP to RAP which triggers such a determination may be determined and updated periodically by the medical service provider (e.g., after examination performed on the patient). In other words, various methods include one or more medical service providers determining the range of "normal" baseline ratios, which will then be used in the medication administration reference table. Alternatively, a generalized set of guidelines may be provided to medical service providers regarding an appropriate baseline.

The method 99 can be adjusted to be more specific in terms of how much a pharmacological, or medication regimen needs to be increased or reduced, which can be varied based on how much the LAP and RAP are trending above or below the normal level. This may be done by implementing another table or set of guidelines within the table 100 that indicates the amount of medication to be administered (e.g., so that a treatment dosage may be adjusted for a patient without requiring direct medical service provider intervention). The table 100 can include any of a variety of medical recommendations/indications, such as beta-blockers and inotropes, for example, as indicated by a particular set of physiologic measurements and associated guidance of the table 100. Furthermore, to inform the patient on which medication to choose and its dosage, the type of medication (e.g. diuretic or vasodilator) that needs to be administered and the dosage thereof can be displayed on, for example, the screen of a computer or a display of a smart device used by the patient.

As referenced above, the measurement data and associated monitoring and treatment methodology is not necessarily limited to LAP and RAP measurements. In some examples, additional or alternative locations (e.g., pulmonary arteries, ventricles, pulmonary veins, aorta, and others) and/or additional or alternative metrics (e.g., temperature and/or oxygen saturation) may be utilized in implementing a monitoring and treatment method such as the method 99.

As explained above, the method 99 may be performed manually or may be partially or completely automated using any device capable of receiving and processing the measurement data from the measurement device 41. For example, the method 99 may be implemented entirely in the monitoring system 72 (e.g., such as a smart device), which performs all the comparisons, calculations, and determinations after receiving the LAP and RAP measurement data from the measurement system 41. In some examples, the method may be implemented partially in the monitoring system 72 and partially in the communications relay 70 which may include a processing unit to receive the LAP and RAP measurement data from the sensors, determine whether the LAP and RAP are above/at/below normal level and decreasing/steady/increasing, then relay this information to the remote device 72 to perform the rest of the method. In yet another example, the subcutaneous implant 83 may be programmed to perform a portion or the entirety of the method.

In still further examples, the method 99 may be implemented in a device with a user interface allowing the patient to administer medications according to the results of the method. The method may also be implemented in the medical service providers' electronic health record (EHR) or electronic medical record (EMR) systems which keep track of the necessary records of each patient. As such, the EHR or EMR systems may use local or remote database to access, among other things, the patient's history of LH or RH/biventricular failure and whether the medical service providers have deemed the patient to be at a risk of such failure. The resulting data from the method may be displayed on a dashboard of the user interface with multiple options for the user (e.g. patient and medical service providers), which may include: LAP and RAP averages, trend arrows, line graphs over time, and waveforms, as well as a history of the medications taken by the patient, etc. The dashboard may also be configured such that the user can first pull up the most meaningful information, such as the averages and trends, then dig in further for a more detailed analysis, such as the waveforms. This may be implemented by organizing the multiple options in a hierarchical manner based on the importance of each option. In one example, this hierarchical order of the options is customizable according to the user's preference, such that the most preferred information can be pulled up first.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical treatment system for determining administration of medications to a patient, the system comprising:
    a plurality of sensors configured to perform a first set of physiologic measurements in a right side of the heart and a second set of physiologic measurements in a left side of the heart; and
    a receiver configured to receive measurement data regarding the first and second sets of physiologic measurements, to receive patient condition data representative of at least one patient condition from the group of left heart failure, right heart failure, or biventricular failure, and to output to a display device the received measurement data;
    a memory unit configured to store the received measurement data and the received patient condition data; and
    a controller configured to:

determine, based on the received measurement data, measurement trends including whether each of the first and second sets of measurements is trending below a normal level, trending at a normal level, or trending above a normal level; and determine a treatment regimen for the patient based on the received patient condition data and the determined measurement trends.

2. The medical treatment system of claim 1, wherein the controller is further configured to determine whether to modify a pharmacologic treatment regimen based upon the received measurement data.

3. The medical treatment system of claim 1, wherein the controller is coupled to an implantable measurement device.

4. The medical treatment system of claim 1, wherein the controller is associated with a monitoring system configured to be located external to the patient.

5. The medical treatment system of claim 1, wherein the physiologic measurements include blood pressure measurements.

6. The medical treatment system of claim 1, wherein the physiologic measurements include at least one of blood temperature and oxygen saturation measurements.

7. A method of assessing a heart failure status of a patient, the method comprising:

receiving, by a monitoring system, first measurement data based on a first set of physiologic measurements performed in a right side of a heart of the patient, wherein the first measurement data is transmitted from an implanted measurement system;

receiving, by the monitoring system, second measurement data based on a second set of physiologic measurements performed in a left side of the heart, wherein the second measurement data is transmitted from the implanted measurement system; and receiving, by the monitoring system, patient condition data representative of at least one patient condition from the group of left heart failure, right heart failure, or biventricular failure;

outputting, to a display device, the received first and second measurement data;

determining, by the monitoring system based on the received measurement data, measurement trends including whether each of the first and second sets of measurements is trending below a normal level, trending at a normal level, or trending above a normal level; and determining, by the monitoring system, a treatment regimen for the patient based on the received patient condition data and the determined measurement trends.

8. The method of claim 7, further comprising determining whether to modify a pharmacologic treatment regimen based upon the received first and second measurement data.

9. The method of claim 7, wherein the implanted measurement system comprises a plurality of sensors, and the first and second sets of physiologic measurements are performed using the plurality of sensors.

10. The method of claim 7, wherein the physiologic measurements include blood pressure measurements.

11. The method of claim 7, wherein the physiologic measurements include at least one of blood temperature and oxygen saturation measurements.

12. The method of claim 10, wherein the sensors perform the blood pressure measurements in the left and right atria.

13. The method of claim 7, further comprising:

displaying, based on the determination of how the first and second sets of physiologic measurements are trending, an instruction on what recommended medication(s) to administer and the dosage thereof.

14. A method of informing changes to the pharmacologic management of a patient comprising:

obtaining, by a monitoring system, first measurement data based on a first set of hemodynamic measurements representing the right side filling pressure of the heart of the patient, wherein the first measurement data is transmitted from an implanted measurement system;

obtaining, by the monitoring system, second measurement data based on a second set of hemodynamic measurements representing the left side filling pressure of the heart of the patient, wherein the second measurement data is transmitted from an implanted measurement system; and obtaining, by the monitoring system, patient condition data representative of at least one patient condition from the group of left heart failure, right heart failure, or biventricular failure;

determining, by the monitoring system, based on the first and second measurement data, measurement trends including whether each of the first and second sets of physiologic measurements is: trending below a normal level, trending at a normal level, or trending above a normal level; and determining, by the monitoring system, a treatment regimen for the patient based on the obtained patient condition data and the determined measurement trends.

15. The method of claim 14, wherein the patient is suffering from heart failure, kidney failure, or both.

* * * * *